(12) United States Patent  (10) Patent No.: US 8,717,576 B2
Hacker  (45) Date of Patent: May 6, 2014

(54) SHORT COHERENCE INTERFEROMETER

(75) Inventor: Martin Hacker, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 796 days.

(21) Appl. No.: 12/680,722

(22) PCT Filed: Sep. 26, 2008

(86) PCT No.: PCT/EP2008/008230
§ 371 (c)(1),
(2), (4) Date: Jul. 16, 2010

(87) PCT Pub. No.: WO2009/043557
PCT Pub. Date: Apr. 9, 2009

(65) Prior Publication Data
US 2010/0284021 A1 Nov. 11, 2010

(30) Foreign Application Priority Data
Sep. 28, 2007 (DE) .................. 10 2007 046 507

(51) Int. Cl.
G01B 9/02 (2006.01)
(52) U.S. Cl.
USPC ........................................ 356/479
(58) Field of Classification Search
USPC ......... 356/451, 453, 456, 491, 479, 497, 503, 356/504; 250/227.19, 227.27
See application file for complete search history.

(56) References Cited

U.S. PATENT DOCUMENTS

| 4,938,584 | A | 7/1990 | Suematsu et al. |
| 5,321,501 | A | 6/1994 | Swanson et al. |
| 5,795,295 | A | 8/1998 | Hellmuth et al. |
| 6,198,540 | B1 | 3/2001 | Ueda et al. |
| 6,654,127 | B2 | 11/2003 | Everett et al. |
| 6,806,963 | B1 | 10/2004 | Wälti et al. |
| 7,084,986 | B2 | 8/2006 | Hellmuth et al. |

(Continued)

FOREIGN PATENT DOCUMENTS

| DE | 10 2005 058 220 A1 | 6/2007 |
| EP | 1 602 320 A1 | 12/2005 |

(Continued)

OTHER PUBLICATIONS

Chen, S., et al., "A Compact Optical Device for Eye-Length Measurement," *IEEE Photonics Technology Letters*, vol. 5, No. 6, pp. 729-731 (Jun. 1993).

(Continued)

*Primary Examiner* — Gregory J Toatley
*Assistant Examiner* — Dominic J Bologna
(74) *Attorney, Agent, or Firm* — Patterson Thuente Pedersen, P.A.

(57) ABSTRACT

A short coherence interferometer apparatus for measuring multiple axially spaced regions of a specimen, in particular the eye, which has at least one measuring beam path, through which multiple individual measuring beams are incident on the specimen, and one reference beam path, through which a reference beam runs, with which the individual measuring beams are superimposed and brought into interference. The individual measuring beams are axially offset to one another upon incidence on the specimen by an amount which is adapted to the axial spacing. The interferometer apparatus superimposes each individual measuring beam with the reference beam in an interfering manner and conducts it to a detector associated with the particular individual measuring beam. The individual measuring beams are combined into a mixture in which they have varying phasing in the superposition with the reference beam.

28 Claims, 14 Drawing Sheets

(56) References Cited

U.S. PATENT DOCUMENTS

| | | | |
|---|---|---|---|
| 7,126,693 B2 | 10/2006 | Everett et al. | |
| 7,631,970 B2 | 12/2009 | Wei | |
| 2004/0061830 A1* | 4/2004 | Hellmuth et al. | 351/205 |
| 2004/0239943 A1 | 12/2004 | Izatt et al. | |
| 2005/0140981 A1* | 6/2005 | Waelti | 356/479 |
| 2006/0109477 A1* | 5/2006 | Zhou et al. | 356/479 |
| 2006/0114472 A1* | 6/2006 | Tatam et al. | 356/479 |
| 2006/0171503 A1 | 8/2006 | O'Hara et al. | |
| 2008/0285043 A1* | 11/2008 | Fercher et al. | 356/451 |
| 2009/0268209 A1 | 10/2009 | Waelti et al. | |
| 2013/0128274 A1 | 5/2013 | Yun et al. | |

FOREIGN PATENT DOCUMENTS

| | | |
|---|---|---|
| JP | 2007-101365 | 4/2007 |
| JP | 2007-510143 | 4/2007 |
| WO | WO 01/33820 A1 | 5/2001 |
| WO | WO 03/086180 A2 | 10/2003 |
| WO | WO 2004/111661 A2 | 12/2004 |
| WO | WO 2005/077256 A1 | 8/2005 |
| WO | WO 2006/053669 A1 | 5/2006 |
| WO | WO 2007/039267 A2 | 4/2007 |
| WO | WO 2007/053971 A1 | 5/2007 |
| WO | WO 2007/065670 A2 | 6/2007 |
| WO | WO 2007/084750 A2 | 7/2007 |

OTHER PUBLICATIONS

Podoleaunu, Adrian, "Unbalanced versus balanced operation in an optical coherence tomography system," *Applied Optics*, vol. 39, No. 1, pp. 173-182 (Jan. 1, 2000).

Baumgartner, Angela, et al., "Resolution-improved dual-beam and standard optical coherence tomography: a comparison," *Graefe's Arch Clin Exp ophthalmol*, vol. 238, No. 5, pp. 385-392 (2000).

Yun, S.H., et al., "Motion artifacts in optical coherence tomography with frequency-domain ranging," *Optics Express*, vol. 12, No. 13, pp. 2977-2998 (Jun. 28, 2004).

* cited by examiner

SHORT COHERENCE INTERFEROMETER

PRIORITY CLAIM

The present application is a National Phase entry of PCT Application No. PCT/EP2008/008230, filed Sep. 26, 2008, which claims priority from German Application Number 102007046507.8, filed Sep. 28, 2007, the disclosures of which are hereby incorporated by reference herein in their entirety.

FIELD OF THE INVENTION

The invention relates to a short coherence interferometer apparatus for measuring multiple axially spaced regions of a specimen, in particular the eye, which apparatus has at least one measuring beam path, through which multiple individual measuring beams are incident on the specimen, and one reference beam path, through which reference radiation is guided, which is superimposed with the individual measuring beams and is brought into interference with the individual measuring beams, wherein the individual measuring beams are axially offset to one another upon incidence on the specimen by an amount which is adapted to the axial spacing, and wherein the interferometer apparatus has a superposition device, which superimposes each individual measuring beam returning from the specimen with the reference radiation to cause interference.

Furthermore, the invention relates to a short coherence interferometer apparatus for measuring multiple axially spaced regions of a specimen, in particular the eye, which apparatus has at least one measuring beam path, through which multiple individual measuring beams are incident on the specimen, wherein the individual measuring beams are axially offset to one another upon incidence on the specimen by an amount which is adapted to the axial spacing, and wherein the interferometer apparatus superimposes at least two of the individual measuring beams with one another to cause interference.

Such short coherence interferometer apparatuses for optical imaging using optical coherence tomography are known, for example, from WO 2007/065670 A1. The first-mentioned type causes interference of each of multiple measuring beams with a separate reference beam, the second-mentioned type superimposes multiple individual measuring beams in pairs and is also designated as a so-called "dual beam" interferometer.

Optical coherence domain reflectometry (OCDR) is used for the purpose of detecting the location and size of scattering centers inside a specimen, such as miniaturized optical components or biological tissue, such as the human eye. Reference is made to US 2006/0109477 A1 for an overview of corresponding literature on optical coherence tomography and in particular on optical coherence domain reflectometry. This patent application, which inter alia originates from the inventor of the present invention, also deals with the fundamental principle of optical coherence tomography. The variants of time domain OCDR (TD OCDR) using rapidly scanning reference arms and Fourier domain OCDR (FD OCDR) using a fixed reference arm and analysis of spectral interference, are known for OCDR. FD OCDR is differentiated once again into a species employing broadband light sources and spectrometer-based detection (spectral domain or SD OCDR) and a species employing spectrally swept light sources and broadband detectors (swept-source or SS OCDR).

Optical coherence tomography, in particular in the form of FD OCDR, is problematic in the fixed linkage of measuring area and measuring resolution. Many publications are known in the prior art which deal with measurement of objects in regions which are geometrically larger by multiple orders of magnitude than the desired resolution. An example of such a measuring task is the measurement of regions on the human eye, e.g., the detection of structures both in anterior parts of the eye, for example, on the cornea, and also on the retina.

One approach for eye measurement both in anterior parts of the eye and also in the ocular fundus is known from WO 2007/065670 A1, which combines multiple interferometer apparatuses in a skillful manner, which are each constructed from a separate reference arm and an associated measuring arm. By varying tuning of these multiple independent interferometer apparatuses, which are combined into one device, measurement can be performed simultaneously at various points in the eye. The publication describes various approaches for differentiating the radiations in the combined interferometers, for example, in regard to the polarization of the radiation or its wavelength.

One such type of differentiation is also described in WO 01/38820 A1, which is only relates to FD OCDR, however, i.e., it requires moving elements for adjusting the reference arm length. The principle of using multiple reference arms of varying length is also found in US 2005/0140981, or U.S. Pat. No. 6,198,540, which each relate to OCDR and use multiple, individually tuned reference beam paths of different lengths.

Finally, US 2006/0109477, which was already cited at the beginning, does not allow multiple differently axially spaced regions of a specimen to be detected at all, but rather relates to the greatest possible sensitivity, for which 3×3 phase couplers are used in combination with a differential signal analysis, i.e., balanced detection.

SUMMARY OF THE INVENTION

From this prior art, the invention is therefore based on the object of providing a short coherence interferometer apparatus, which can detect multiple axially spaced regions of a specimen, the regions being able to be spaced apart further than allowed by the measuring area resulting from the parameters of the OCDR variant used, such as the spectral resolution in FD OCDR, wherein a particularly high sensitivity further shall be provided, i.e., even points in the specimen which only backscatter weakly can be detected.

This object is achieved according to the invention by a short coherence interferometer apparatus of the mentioned type, in which the superposition device has multiple outputs, each one of which feeds a detector, wherein the superposition device receives the same reference radiation for superposition, and outputs a mixture of the multiple individual measuring beams superimposed with the reference radiation at each output, each mixture containing fractions of the individual measuring beams, superimposed with the reference radiation in different phasing.

The invention thus employs an interferometer having only one reference arm. This not only results in an advantageous structural simplification. Additionally, a high signal sensitivity is achieved in combination of balanced detection and multiple measuring arms and one common reference arm, because interactions between multiple strong reference signals are prevented. Such interactions would result in strong and wide-ranging artifacts. In the concept according to the invention, at most an interaction of two weak signals occurs, namely the signals from the measuring arms. An interaction of two strong reference signals is avoided.

Furthermore, a reduction of noise components can be achieved, to which components the reference light component significantly or primarily contributes, such as shot noise. If the shot noise is the greatest noise source (shot-noise-limited operation) and the measuring signal is thus small in relation to the reference signal, the signal-to-noise ratio typically corresponds to the count of the detected measuring signal photons, because the signal component corresponds to the product of the counts of interfering measuring and reference light photons, while the noise component is proportional to the count of the reference light photon count.

If the count of the reference light components is increased by the use of multiple reference arms, the noise component rises corresponding to the sum of the reference photons contained in the reference light component. However, the signal component still corresponds only to the product of measuring light photons with the photons of a single adapted reference light component. This means that the signal-to-noise ratio for the individual measuring signals drops.

In contrast, the solution according to the invention, having multiple measuring signals adapted to only one reference arm, allows, at unchanged signal levels, to limit the noise to the contribution caused only by the one reference light component.

Thus, for example, as is typical in the prior art, if two measuring signals are measured using two identical reference signals adapted individually to the measuring signals, the shot-noise-limited signal-to-noise ratio is worse by a factor of 2 or 3 dB in relation to the use of only one reference signal, to which the two measuring signals are individually adapted.

In a dual-beam variant, the object is further achieved by a short coherence interferometer apparatus for measuring multiple axially spaced regions of a specimen, in particular the eye, which apparatus has at least one measuring beam path, through which multiple individual measuring beams are incident on the specimen, wherein the individual measuring beams are axially offset to one another upon incidence on the specimen by an amount which is adapted to the axial spacing, and wherein the interferometer apparatus superimposes at least two of the individual measuring beams with one another to cause interference, the interferometer apparatus superimposing each of the two individual measuring beams with the other in an interfering manner and then conducting each of them to an associated separate detector.

The invention thus uses individual measuring beams, which are axially individually delayed so that an interference signal occurs at the associated detector after the superposition device. The individual measuring beams in the mixture were each superimposed using the reference beam to cause interference, the reference beam being superimposed on each individual measuring beam of the mixture in an individually varying phase. This procedure further allows balanced detection in the interferometer apparatus for increasing the sensitivity and/or determining the quadrature component. The advantages of balanced detection for noise suppression are extensively described, for example, in Podoleanu, Appl. Optics 39, 173 (2000), "Unbalanced versus balanced operation in an optical coherence tomography system". Furthermore, axially spaced regions of the specimen, whose spacing is much greater than the axial measuring range of the individual measuring beams, may be detected simultaneously by the separate individual measuring beams.

In doing so, it is possible to adapt the focusing and polarization states, and the dispersion properties of the individual measuring beams to the particular associated axial measuring regions of the specimen, in order to achieve maximum signal qualities. The advantages of targeted adaptation of the dispersion condition in interferometers for Fourier domain optical coherence tomography (FD OCDR) for the purposes of mirror artifact suppression are described in US 2006/0171503, to which the inventor contributed.

The measuring radiation preferably originates from a beam source which is implemented to execute SS OCDR, i.e., is tunable. The invention is generally also possible and can be implemented, however, for SD OCDR (i.e., using spectral analysis of non-swept radiation) and/or TD OCDR (with sweeping of the interference condition in the interferometer, e.g., adjustment of the length of a reference beam path).

The splitting of the individual measuring beams can be performed from a common measuring beam, i.e., after the superposition device has split the measuring beam path and the reference beam path from a source beam which is provided by the beam source. For this variant, a beam source which provides a measuring beam is preferably provided, which beam source outputs a source beam, and it is provided that the superposition device splits divides a certain intensity fraction of the source beam off into the measuring beam path and the reference beam path.

The splitting of the individual measuring beams in the path to the specimen and the re-combination in the return path from the specimen can (only) occur in the measuring beam path. A lens device is particularly advantageously used for this purpose, which splits the measuring radiation into the individual measuring beams, offsets (delays) them axially to one another, and also focuses them on the specimen at different focal lengths.

A particularly compact lens device is obtained if it provides the individual measuring beams using a pupil division, a separate pupil area of the lens device being associated with each individual measuring beam and the optical path lengths and optionally also the imaging properties of the pupil areas being different.

Such a lens device is also possible independently of the described short coherence interferometer apparatus, so that a lens apparatus or device can be provided as an independent invention, which splits a supplied beam bundle into individual beam bundles, delays the individual beam bundles in relation to one another, and optionally also outputs them differently focused, the lens apparatus having a divided pupil, a separate pupil area being associated with each individual beam bundle, and the optical path lengths, dispersions, and optionally also the imaging properties of the lens apparatus or device in the separate pupil areas being different.

A refinement (which is also possible in the scope of the short coherence interferometer apparatus, of course), in which the lens apparatus or device has a glass body having two lens surfaces and a hole running along the optical axis in the glass body is implemented on one lens side, is particularly expedient. The depth of the hole is responsible for the mutual delay of the individual beams, because a different optical path length through the glass body thus results for the individual beams. The optical properties of the hole base and the lens surface, into which the hole is introduced, may also differ. Any differences effect varying focusing of the individual beams.

The delay and the focusing of the individual beams are thus settable and/or selected independently of one another in the design of the lens apparatus or device by the independently selectable parameters of hole depth and geometric shape of the hole base and the lens surface.

The possibility is also noted of filling the cavity in the glass body entirely or partially with a material having optical properties different in comparison to the remaining glass body, i.e., in particular index of refraction and dispersion, in order to achieve the desired optical delay and/or dispersion conditions.

An alternative to generating the individual measuring beams from a common measuring beam, i.e., after splitting of the reference beam path, is that the superposition device splits the individual measuring beams directly from the source beam.

Generally it is preferable to perform the splitting of the beams at the superposition device according to specific intensity ratios, i.e., not to perform a polarization separation, as is found at many points in the prior art, for two reasons: on the one hand, polarization splitters are costly components, and thus make an apparatus more expensive. On the other hand, it must subsequently be ensured again with great effort that the polarization-split individual measuring beams have the same polarization state again upon superposition. This is problematic in particular in specimens in which the polarization state of an individual measuring beam is possibly changed by double-refracting structures of the specimen, for example, upon the passage through the lens in the eye. Finally, a polarization separation is also regularly limited to at most two split beams, while in contrast intensity splitting, as is possible using fiber couplers, for example, can also generate more than two split beams.

It is therefore preferable in a refinement of the invention that the measuring beam path has individual measuring beam paths of different lengths for the individual measuring beams and the superposition device splits specific intensity components of the source beam into the individual measuring beam paths. The superposition device can optionally also split a specific intensity component of the source beam into the reference beam path.

The splitting of the original beam into the individual measuring beams and (if not using the dual-beam version) the reference beam, can be performed according to intensity rations particularly simply using a 3×3 fiber coupler or two combined 2×2 fiber couplers, as it is described, for example, in already cited US 2006/0109477 A1 to which one of the inventors of the present application contributed. The content of the disclosure of this publication is expressly incorporated here by reference in regard to the mode of operation, the construction, and the capabilities of such fiber couplers.

The superposition device outputs a mixture of at least two individual measuring beams at each of its outputs, which measuring beams are each superimposed with the reference beam, wherein an individual phase shift is caused for each individual measuring beam at superposition with respect to the reference beam, which individual phase shift has the result that the individual measuring beams experience a different relative phasing to the reference beam upon the superposition. If the mentioned 2×2 fiber couplers are used, the phase shift is 180°, for example, whereby balanced detection, as previously described, may be implemented particularly advantageously.

Each detector thus receives a mixture of multiple individual measuring beams, each superimposed with the reference beam using different relative phasing. The individual measuring beams may have essentially contribute equal to the mixture, but an asymmetrical composition is also possible in the mixture, in which one of the individual measuring beams in the mixture has a disproportional fraction, in particular greater than 90%. This increase in fraction is at the cost of the other individual measuring beam or beams, of course.

The simultaneous detection of the measurement region signals allows in spacing measurements a compensation of position errors which result from any axial specimen movement. The otherwise negative effects of axial specimen movements on FD OCT are described, for example, in Yun et al., Opt. Express 12, 2977 (2004), "Motion artifacts in optical coherence tomography with frequency-domain ranging".

Optionally, a blocking element can be provided, which shadows individual, multiple, or all individual measuring beams except one, so that only one individual measuring beam is still superimposed with the reference beam, if the blocking element is activated.

A particularly high detection precision is achieved if the superposition of the individual measuring beams (either with the reference beam or, in the case of the dual-beam variant, with at least one other individual measuring beam) shows a loss of less than 50%. In the approaches of the prior art, this feature cannot be implemented, because polarization splitting or spectral splitting causes ever higher losses therein, for example.

A particularly high sensitivity is achieved with differential readout of each two of the detectors. This already mentioned balanced detection is also described in US 2006/0109477 A1, the content of whose disclosure is also incorporated by reference in its entirety.

The signal quality at interference and thus the sensitivity at which even weakly scattering objects may be detected in the specimen is a function of the degree of the interference, of course, which the individual measuring beams brought into interference may have at all. The polarization state is significant for this purpose, of course, because orthogonal linearly polarized beams cannot interfere with one another at all, for example, as is known. It is therefore preferable to provide a polarization controller in the measuring beam path which controller is active for all individual measuring beams and equalizes the polarization states of the individual measuring beams to one another and/or equalizes them to the polarization state of the reference beam before the superposition of the individual measuring beams (if the dual-beam version is not used). Faraday rotators may also be used in the individual measuring beams and in the reference arm, in order to implement an automatic adaptation of the polarization states upon the superposition. Faraday rotators in the specimens and reference arm of an OCT interferometer are described in U.S. Pat. No. 7,126,693.

With pupil splitting of a measuring beam into individual measuring beams and sufficiently uniform influence of the specimen on the polarization states of the individual measuring beams, a single polarization controller is preferably used for equalizing to the polarization state of the reference radiation for the superposition with the individual measuring beams.

For an embodiment in which the individual measuring beams are split directly from the source beam, it is advantageous to provide a polarization controller in each individual measuring beam path generated in this manner, so that the polarization controllers thus provided equalize the polarization states of the individual measuring beams to one another before the superposition of the individual measuring beams. In contrast to a central polarization controller in one part of the measuring beam path, in which all individual measuring beams still propagate in common, an individual adaptation of the polarization states for each individual measuring beam can now be performed. The equalization is also again oriented to the polarization state of the reference beam path, if no dual-beam version is used.

In one embodiment the described apparatus is particularly preferably implemented for OCDR using a swept radiation source (SS OCDR), of course, because of which a corresponding embodiment is preferred.

The apparatus allows a specimen to be detected in regions which are spaced axially further apart than permitted by the measuring range, which is predetermined, for example, in SS OCDR by the spectral line width of the swept radiation source, in TD OCDR by the adjustment path of the reference arm of the interferometer, and in SD OCDR by the spectral resolution of the detection. It is therefore preferable for the axial offset of the individual measuring beams to be greater than a measuring range given by the swept range of the interferometer apparatus and by the spectral splitting and detection, respectively.

Of course, the variants of the apparatus according to the invention described here may also be implemented for lateral scanning of a specimen, in particular for imaging. For this purpose, at least one scanning device is provided for scanning the specimen by lateral mutual displacement of specimen and at least one of the individual measuring beams.

The scanning device is thus effective for at least one of the individual measuring beams. For application on the eye, imaging of the eye lens is thus preferably also performed, including the determination of its shape and location (tilt of the lens, i.e., angle between optical axis and axis of vision, curvature of the posterior lens surface, curvature of the anterior lens surface). Imaging in the area of the retina is also possible, in particular in the region of the fovea.

The scanning device for at least one of the individual measuring beams advantageously also allows a combined measurement, which goes beyond simple spacing measurement or topography detection. If one measures a moving object, such as the human eye, there is always the problem that eye movements during the measuring procedure result in corruption. This is particularly unfortunate when scanning using optical coherence tomography. The apparatus according to the invention allows one of the individual measuring beams to be used to detect the distance to a reference point, such as the corneal apex or the retina base, and to obtain a measure of the movement of the specimen, such as the eye, from any distance changes. The movement of the reference point can then be used to correct the measured data obtained from simultaneous lateral scanning of another area of the specimen.

In one embodiment of this approach, not only the axial location of the reference point, but rather also its lateral location are detected. For example, the lateral movement of the corneal apex. A correction is then possible not only in regard to an axial displacement of the studied specimen, but rather also in regard to lateral displacements. The reference point for a three-dimensional imaging, which is performed by scanning another area of the object, can be tracked three-dimensionally and the corresponding measured data can be corrected three-dimensionally in regard to movement of the reference point.

In one embodiment the apparatus has a corresponding control unit, which performs the previously described referencing by detection of the axial location of a reference point using an individual measuring beam or by detection of the three-dimensional location of the reference point by using an independently scanned individual measuring beam, and controls the apparatus.

It is obvious that if not noted to the contrary, the above-mentioned features or properties and the features or properties to be explained hereafter of embodiments can be utilized not only in the disclosed combinations, but rather also in other combinations or optionally alone, without leaving the scope of the present invention. A suitable control unit is provided for executing any method steps in the apparatus. It is also to be noted that a following description on the basis of SS OCDR is no restriction to this OCDR principle. The invention is similarly also suitable for SD OCDR or TD OCDR. Of course, the sweeping of the source, as occurs in SS OCDR, is replaced by a spectral analysis of the superimposed radiation or by an adjustment of the reference beam path, respectively.

BRIEF DESCRIPTION OF THE DRAWINGS

The invention is explained in greater detail hereafter for exemplary purposes with reference to the appended drawings, which also disclose features essential to the invention. In the figures.

DETAILED DESCRIPTION

Figure 1:
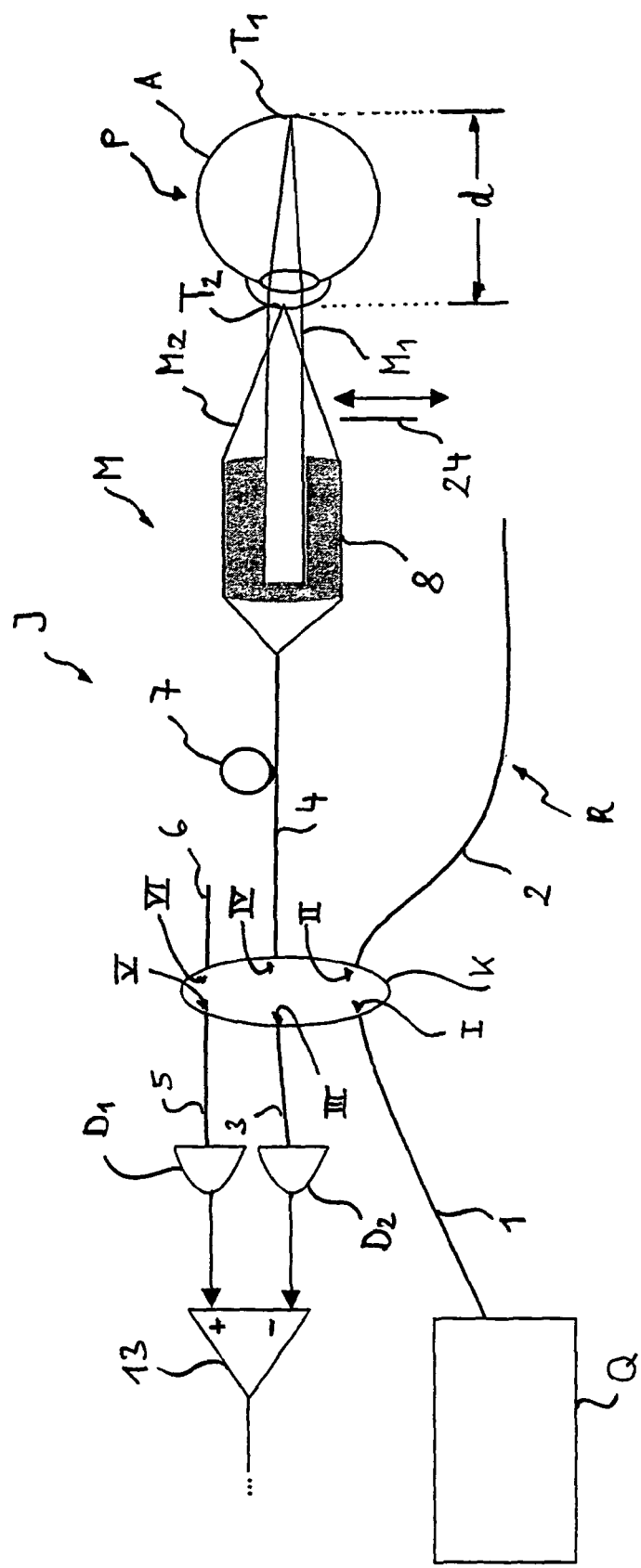
FIG. 1 depicts an SS OCDR interferometer having balanced detection for the simultaneous detection of two different areas of an eye.

FIG. 1 schematically shows an interferometer for SS OCDR. Radiation from a beam source Q, which is swept and has a line width of less than 30 pm, for example, preferably ≤26 pm or in another embodiment preferably <15 pm or even ≤13 pm. Such beam sources are known in the prior art and are described, for example, in US 2006/0109477 A1, which was already noted at the beginning. Reference is therefore made to this document in this regard. The interferometer I is used for the purpose of detecting different subregions $T_1$ and $T_2$ on a specimen P, which is an eye A in the example embodiment. Instead of an eye, of course, any arbitrary, non-biological technical structure may also be detected using the interferometer I, because the interferometer I generally detects the location and scattering intensity of scattering centers which are in the subregions $T_1$ and $T_2$. Insofar as the present description thus makes reference to the application on an eye A, this is purely exemplary and is not to be understood as restrictive.

Figure 2:
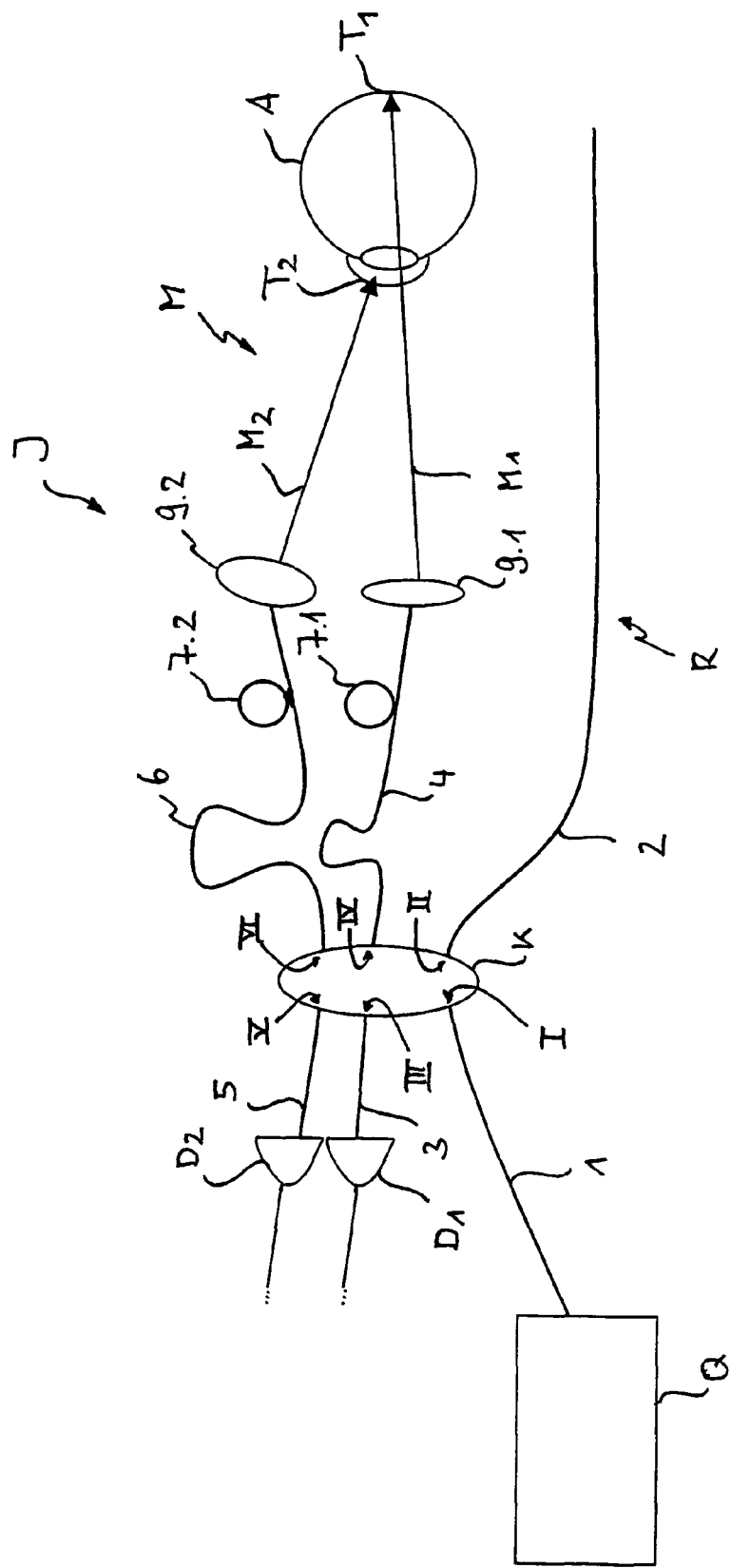
FIG. 2 depicts an interferometer similar to that of FIG. 1, but a measuring beam path of the interferometer of FIG. 1 being altered for greater exploitation of the illumination radiation and extensive individual detection of the measuring radiation from the various areas of the eye being performed.

The subregions $T_1$ and $T_2$ are shown as points in FIGS. 1 and 2. This is only used for a better overview. Due to the sweeping of the radiation source Q, the subregions extend over a range which extends along the axis of incidence of the radiation, of course. However, the maximum measuring depth in SS OCDR, which is limited by the line width of the swept radiation source Q, is not large enough that both the subregion $T_1$ and also the subregion $T_2$ may be detected in one sweeping procedure. The spacing d between the subregions is too wide for this purpose. For example, in measurements on the eye using swept radiation sources, with a central wavelength of approximately 1 µm having a line width in the range between 10 pm . . . 200 pm, scanning depths of approximately 35.2 mm may be implemented, which only corresponds to part of possible eye lengths, because of which multiple axially offset subregions are advantageous for the application on the eye.

The radiation of the laser beam source Q is guided via an optical fiber 1 to a coupler K, which acts as a superposition device and is explained in greater detail hereafter. The coupler K branches off a part of the radiation from the optical fiber 1 into a reference beam path R, which is essentially implemented by an optical fiber 2, at the end of which a mirror device is provided (for example, by terminal reflection of the fiber). Another part of the radiation from the optical fiber 1 is fed into the measuring beam path M beginning with an optical fiber 4.

However, the coupler K not only causes coupling of the radiation of the laser source Q, which thus provides the source beam for the interferometer I, but rather also a distribution and superposition of the measuring radiation returning from the measuring beam path M and the reference radiation returning from the reference beam path R. The coupler K superimposes the reference radiation from the reference beam path R with the measuring radiation from the optical fiber 4 and outputs the superimposed radiation into an optical fiber 3 and in identical fraction, into an optical fiber 5. The signals thus brought into interference are collected by detectors $D_1$ and $D_2$ and are subsequently amplified by means of a balanced detection using a differential amplifier 13.

Because of the physical properties of the coupler K each detector $D_1$ and $D_2$ receives a mixture of the measuring beams superimposed with the radiation from the reference beam path, the individual measuring beams having experienced a relative phase shift between the inputs III and IV of the coupler upon the superposition with the radiation from the reference beam path R. The individual measuring beams are contained in equal fractions in the mixture.

The coupler K is thus active both for the splitting of the original beam and also for the superposition of the reference beam with the measuring radiation. The measuring radiation is composed of individual measuring beams (as explained hereafter). The coupler has terminals I-VI.

Radiation supplied to the terminal I is conducted by the coupler K 80% to the terminal II and 20% to the terminal IV and 0% to the terminal VI, for example, because radiation coupled into the optical fiber 6 is not used further in the present construction.

Measuring radiation returning at the terminal IV is conducted 20% to the terminal I, i.e., back to the source, and 40% in each case to the terminal III and to the terminal V by the coupler K. 80% of the radiation intensity in the measuring beam path is thus utilized for interference.

The radiation which is supplied to the terminal II is conducted 10% to the terminal III, 10% to the terminal V, and 80% to the terminal I.

The interferometer I of FIG. 1 thus uses the radiation from the measuring beam path in a high percentage, but only uses 20% of the intensity which the laser beam source Q feeds into the optical fiber 1. This is quite non-problematical, because it is much simpler to use a high-power laser beam source Q than to compensate for a great measuring signal loss. Because a relatively large intensity excess of the radiation is provided in the reference beam path R due to the construction of the coupler K, this radiation can still be used in another way, for example, for the spectral calibration of the laser beam source Q or for triggering signal recording.

The measuring beam path M begins at the optical fiber 4. It then comprises a polarization controller 7, which ensures that radiation returning from the measuring beam path M is adapted in regard to its polarization properties to the reference radiation, so that maximum interference capability is provided.

The radiation conducted to the specimen P in the measuring beam path M is split from the optical fiber 4 using a monolithic beam splitter 8, which provides the individual measuring beams $M_1$ and $M_2$ already mentioned, which are delayed in relation to each another. The delay is achieved by the monolithic beam splitter 8, which is explained in greater detail hereafter, by different glass paths for the individual measuring beams $M_1$ and $M_2$. The delay is tuned to the spacing d, by which the regions $T_1$ and $T_2$ on the eye A are spaced (from the coupler to the specimen and back). The uniform overall length of the measuring beam path M of this type is tuned to the length of the reference beam path R.

Furthermore, the monolithic beam splitter also causes varying focusing, i.e., it ensures that finally the individual measuring beam $M_2$ is focused in the region $T_2$ and the individual measuring beam $M_1$ is focused in the region $T_1$. This is achieved by the monolithic beam splitter 8, as explained in greater detail hereafter, in that different refraction surfaces are effective for the individual measuring beams $M_1$ and $M_2$ on the output side of the monolithic beam splitter 8.

To be able to shut down one of the individual measuring beams, such as the individual measuring beam $M_1$ or $M_2$, a movable stop 24 is optionally provided as a blocking element, for example, which blocks the particular individual measuring beam. In order to blank out the individual measuring beam $M_1$, the stop 24 is implemented so that it screens out the pupil area in which the monolithic beam splitter 8 provides the individual measuring beam $M_1$. In contrast, a different or additional stop 24 is provided for the individual measuring beam $M_2$, which stop is implemented in the form of a ring screen and only permits the individual measuring beam $M_1$ to pass.

Components which correspond to components which have already been structurally or functionally described are provided with the same reference signs in the figures and are therefore optionally not explained again.

Up to this point, exemplary embodiments for SS OCDR having swept light sources were described. However, if a broadband light source, such as a super luminescence diode (SLD), is used as the radiation source Q and the detectors D are implemented as spectrometers, one obtains a SD OCDR variant of the short coherence interferometer apparatus, which equally has the described advantages. Interferometer apparatuses having multiple spectrometers for quadrature component determination are known from US 2004/0239943. If the broadband source Q is maintained and the reference arm R is implemented so that its optical length can be varied rapidly, a TD OCDR variant of the interferometer apparatus is implemented. A suitable apparatus for rapidly varying the optical length of reference arms (rapid scanning optical delay line, RSOD) is described, for example, in U.S. Pat. No. 6,654,127.

FIG. 2 shows a modified construction of the interferometer of FIG. 1. A greater utilization of the radiation of the laser beam source Q occurs here, so that the construction of FIG. 2 is particularly useful, if safety-motivated limits of the power of the laser beam source Q or boundary conditions, as line width, sweep range, and sweep rate indicate this, i.e., if one wishes to work with lasers having a particularly low power, for example.

Elements of the interferometer I of FIG. 2 which correspond in structure and/or function to those of the interferometer I of FIG. 1 are provided with the same reference signs and are not explained once again. This applies for all figures. The interferometer I according to FIG. 2 differs from the construction shown in FIG. 1 essentially in two aspects. On the one hand, the measuring beam path M is implemented differently. On the other hand, there is no differential readout of the detectors $D_1$ and $D_2$ in the construction shown in FIG. 2 and therefore there is no balanced detection.

The differences in the measuring beam path M are based in the fact that the coupler K couples the source beam of the laser beam source Q from the optical fiber 1 into both the optical fiber 4 (i.e., the terminal IV of the coupler K) and also into the optical fiber VI (i.e., the terminal VI of the coupler K). The generation of the individual measuring beams thus is not performed from a prior common measuring beam, but rather occurs directly at the beam splitter device, in this case the coupler K. The individual measuring beams $M_1$, $M_2$ propagate via a polarization controller 7.1 or 7.2, respectively, as already explained for FIG. 1, which ensures that finally the individual measuring beams have the same polarization direction to one another and above all to the reference beam R after returning from the specimen A. Lenses 9.1 and 9.2 ensure that the individual measuring beams are focused on the particular regions $T_1$ and $T_2$ of the specimen.

The path lengths which the individual measuring beams pass through are equalized to one another, i.e., the optical path length from the terminal IV of the coupler K up to the region $T_1$ is equal to the optical path length from the terminal VI up to the region $T_2$ (and both are also equal to the optical path length of the reference beam path R). This is schematically indicated in FIG. 2 by different loops in the optical fibers 4, 6.

The coupling coefficients of the coupler K are as follows in one example embodiment for the interferometer I of FIG. 2: the distribution of the source beam supplied to the terminal I is 60% to the terminal II and 20% each to the terminals IV and VI. The intensity of the source beam, i.e., the power of the laser beam source Q, is thus exploited 40% and therefore twice as well as in the interferometer I of FIG. 1.

The individual measuring beam $M_1$ returning to the terminal IV is conducted 80% to the terminal III and 20% to the terminal I. A feedback of 0% occurs to the terminal V. This is similarly true for the individual measuring beam $M_2$ at the terminal VI, which is conducted 80% of the terminal V and thus into the optical fiber 5, and 20% back to the source, i.e., to the terminal I and the optical fiber 1. If 0% may only be implemented between the terminals IV and V with disadvantageous effort, a degree of coupling less than or equal to 5% (in particular 4%) can also be used. The degree of coupling between the terminals VI and V then sinks correspondingly from 80%.

The intensity of the individual measuring beams $M_1$ and $M_2$ is thus conducted 80% to the particular associated detectors $D_1$ and $D_2$.

The terminal II is coupled 60% to terminal I, 20% to terminals V and VI, and 20% to terminals III and IV.

The individual detection by means of the detectors $D_1$ and $D_2$ allows the particular scattering intensity to be detected in the region $T_1$ or $T_2$, respectively, without interfering influences from the particular other region. The energy allocation via the coupler K is particularly advantageous if one starts from a laser radiation upper limit at the specimen of 2 mW at the wavelength of 1.05 µm and if the source delivers 5 mW. The described symmetrical distribution of the radiation to the terminals III and V, to which the detectors $D_1$ and $D_2$ are connected via the optical fibers 3 and 5, is then optimal.

The coupler K of FIG. 2 also has the property of the coupler already described in connection with FIG. 1, of superimposing the optical radiation at the inputs IV and VI with the radiation from the reference beam path at the input II at different relative phasings and relaying it as a mixture in each case to the inputs V and III, of course. Thus, it is also mixed at the output V here: the signal at the terminal VI is superimposed with the signal at the terminal II and the signal at the terminal IV is superimposed with the signal at the terminal II. At both terminals VI and IV the signals in the mixture are superimposed with the reference radiation from the terminal II in different relative phasings.

In contrast to the coupler K of FIG. 1, the coupler of FIG. 2 causes an asymmetrical mixture, however, in which the signal from one of the terminals VI or IV has a disproportional fraction in the mixture, in particular greater than 90% or 95%. This results, in the construction of FIG. 2, in the signal from the optical fiber 6 being contained in optical fiber 5 superimposed with the reference radiation at 90% or 95%, while the signal from the optical fiber 4 superimposed to the reference radiation in a different relative phasing is only contained at 10% or 5%. This is similarly true for the optical fiber 3, which predominantly conducts the superimposed signal from the optical fibers 4 and 2. FIG. 2 thus shows an example for an unequally composed mixture at the outputs V and III of the coupler K.

Figure 3:
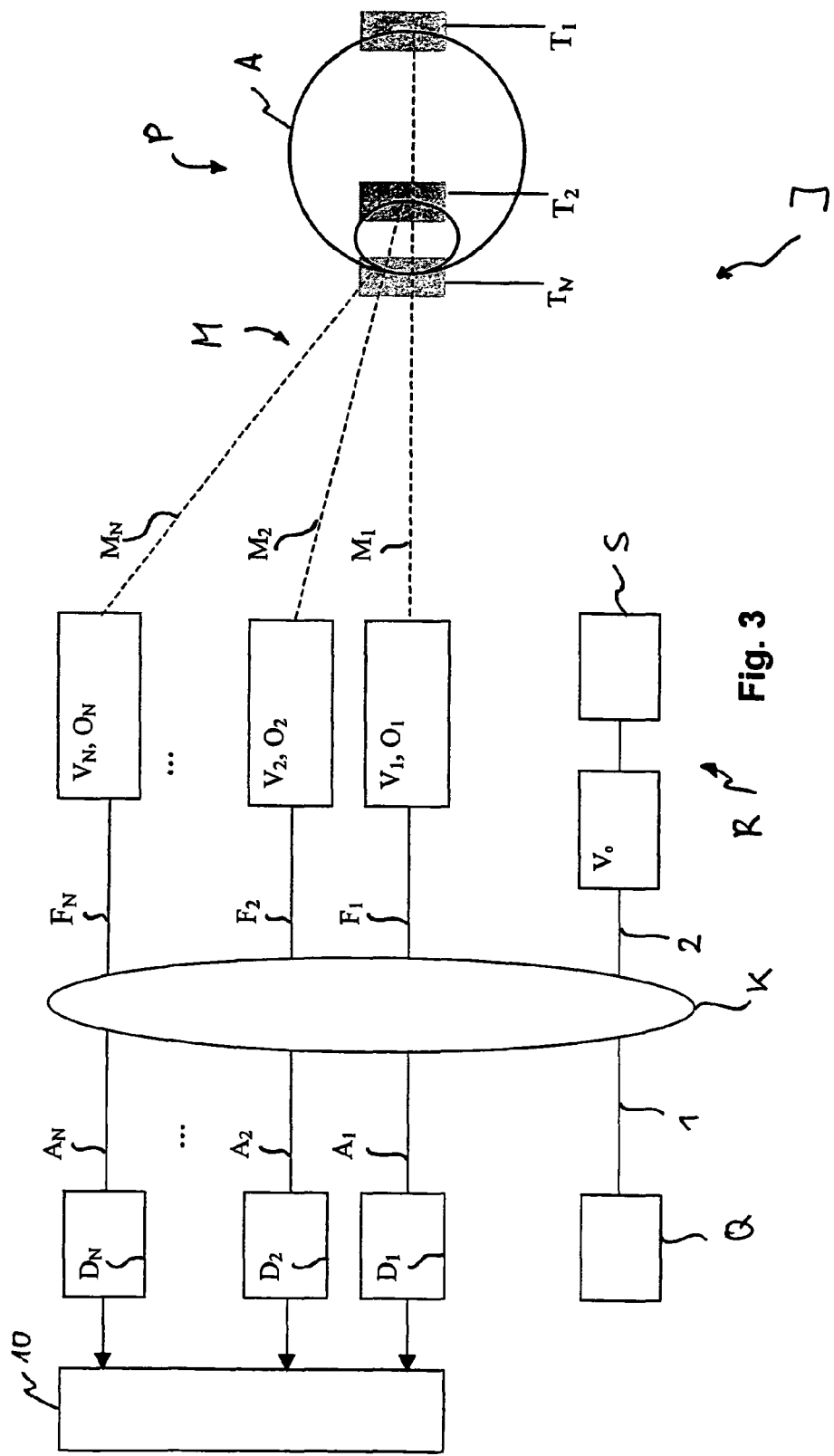
FIG. 3 depicts a schematic illustration of an interferometer similar to that of FIG. 2.

FIG. 3 shows the interferometer structure of FIGS. 1 and 2 in a schematic illustration. In the schematically illustrated interferometer I, the reference sign v designates a delay route, the reference sign O designates an optic, the reference sign F designates a fiber, and the reference sign A designates an output. The particular indices associate these variables to the particular individual measuring beams, as already performed on the basis of FIGS. 1 and 2 for the detectors D and the individual measuring beams M. This applies equally in regard to the regions $T_1$, $T_2$, ..., $T_N$, which are detected on the specimen P.

Using the fiber coupler K, which can also be implemented by a combination of multiple couplers, a part of the original beam provided by the laser radiation source Q in the optical fiber 1 is split for the individual measuring beams $M_1$, $M_2$, ..., $M_N$ into optical fibers $F_1$, $F_2$, ..., $F_N$. An individual delay $v_1$, $v_2$, ..., $v_N$ occurs in each individual measuring beam path thus achieved via optical means, so that the optical path length from the coupler K up to the particular region $T_1$, $T_2$, ..., $T_N$ of the specimen is equal for all individual measuring beams $M_1$, $M_2$, ..., $M_N$. Corresponding optics $O_1$, $O_2$, ..., $O_N$ in the individual measuring beam paths illuminate the subregions $T_1$, $T_2$, ..., $T_N$ to be detected, absorb back-scattered light, and relay it to the fibers F and the coupler K.

The delays v are designated independently of the optics O in the schematic view of FIG. 3. The order, e.g., sequence of delay v and optic O is independent, inter alia, the delays v may also occur in the optics O. Of course fibers F having different delays and/or different lengths may also cause the delays.

The construction of the measuring beam path M is selected for each individual measuring beam $M_1, M_2, \ldots, M_N$ so that the individual measuring beams returning to the coupler K are capable of interference with the radiation from the reference beam path R, i.e., in particular have a sufficiently similar polarization state. Possible polarization controllers are not shown in FIG. 3.

The delay lines are selected, on the one hand, as already explained on the basis of FIGS. 1 and 2, so that the optical path lengths for all individual measuring beams from the coupler K up to the region of the specimen to be detected are equal. However, they are also selected (this also applies for FIGS. 1 and 2, of course), so that the optical path length of individual measuring beams is equalized to that of the reference beam in the reference beam path R, because only then interference of superimposed individual measuring beams and reference beam is possible. This superposition is performed by the coupler K, and it feeds the individual measuring beams $M_1, M_2, \ldots, M_N$, which are superimposed with a fraction of the reference beam and are brought into interference, into the particular outputs $A_1, A_2, \ldots, A_N$, where they are recorded by corresponding detectors, which are read out by an analysis unit 10. Because the coupler K again conducts a mixture of the individual measuring beams, each superimposed with the reference radiation in different relative phasing, to the outputs $A_1, A_2, \ldots, A_N$, of course, the mixture can turned from equal fractions (and optionally performed differential readout for balanced detection) up to greatly disproportional fractions of one or more individual measuring beams. As far as any specific splits, fractions, or mixture compositions are described here, they are not to be understood as restrictive, but rather as solely exemplary.

The schematic illustration of the interferometer I in FIG. 3 clarifies that the illustration in FIGS. 1 and 2 having two individual measuring beams is not restrictive. Rather, the number of the individual measuring beams can be selected arbitrarily and the upper limit for N does not have to be 2.

Of course, one of the delays can also be replaced by a correspondingly set distance to the specimen P or the length (e.g., to the mirror S) in the reference beam path. A further reduction in the number of the delay lines can be achieved by limiting the spacings of the regions T in connection with an increased scanning depth of the laser beam source Q.

In order to ensure the desired high efficiency of the detection of each individual measuring beam, the coupler K is designed so that for all outputs to fibers F, a coupling is provided between the original beam, i.e., the fiber 1, and the particular fiber F of less than 50%.

The interferometer I achieves for the constructions described here the high efficiency of the analysis of the individual measuring beams in that the beam splitter device couples with respect to intensity asymmetrically the source beam into the reference/measuring beam path and the measuring beam path into the detector feeds. In particular, the degree of coupling with which the source beam is split into the individual measuring beam paths can be reduced to less than 50%, in order to achieve in the opposite direction a coupling between the individual measuring beam paths and the feeds to the associated detectors of greater than 50%.

Figure 4:
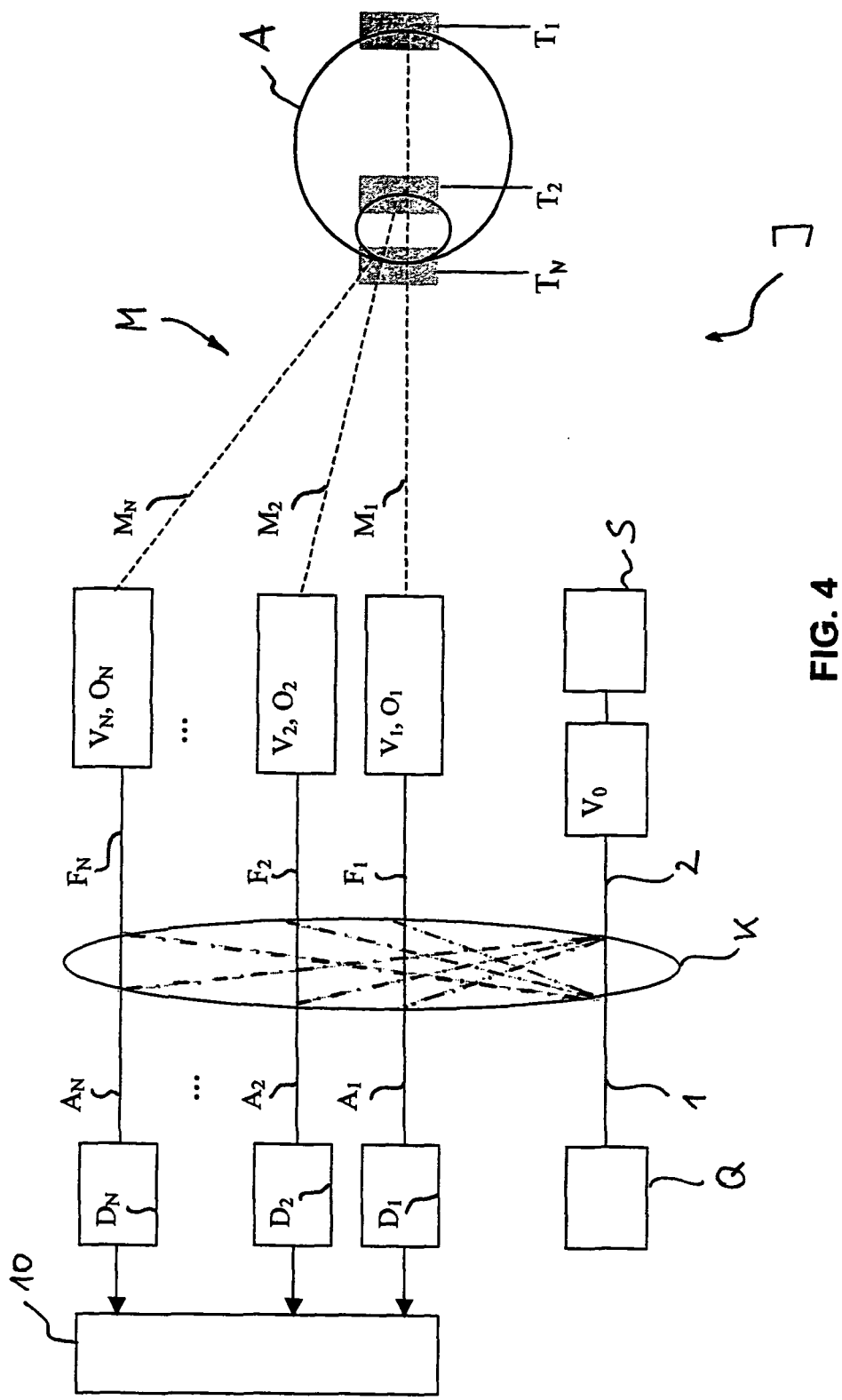
FIG. 4 depicts an illustration similar to that of FIG. 3 with the clarification of the effect of a beam splitter device.

The individual coupling coefficients in the coupler K may be implemented in still other ways. FIG. 4 shows an example, in which solid lines designate a total degree of coupling of 80% and dot-dash lines designate a total degree of coupling of 20%. The total degree of coupling is the sum of the degrees of coupling for all correspondingly marked outgoing beams at this output. The radiation from the optical fiber 1, which guides the source beam, is thus coupled 80% to the optical fiber 2 and the total degree of coupling to the optical fibers F is 20%. Each individual optical fiber F contains an equal part of this 20% fraction. The particular coupling between F and A, i.e., the transmission of the individual measuring beam upon superposition with the reference beam to the particular detector can be at most 1 minus the total degree of coupling, with which the source beam is distributed to the fibers. By reducing this degree of coupling a very high signal intensity can be achieved at the detectors, so that predominantly separated signals are detected for the subregions.

Figure 5:
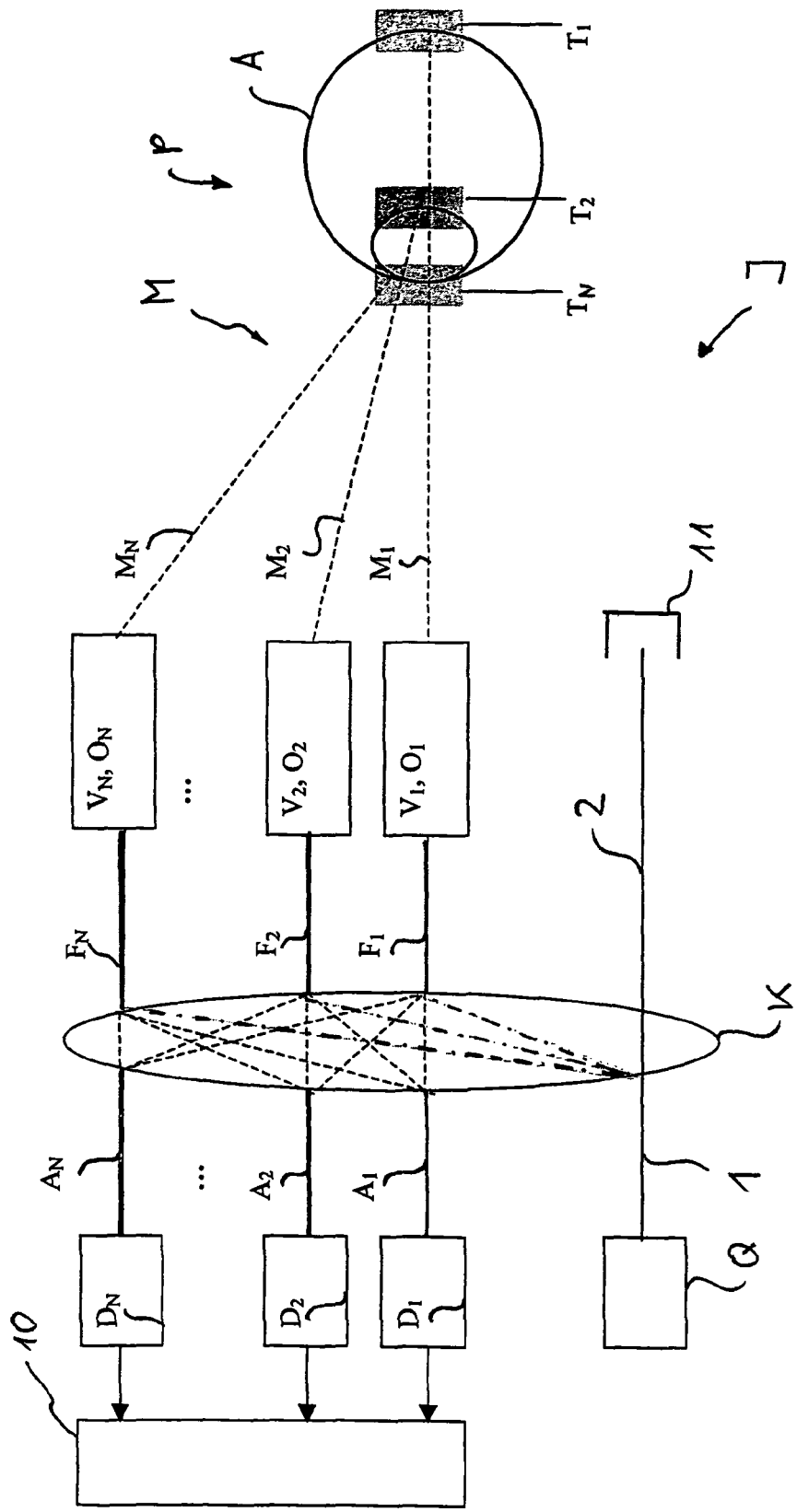
FIG. 5 depicts an interferometer illustration similar to that of FIG. 4, but in an embodiment of a dual-beam interferometer.

The construction of FIG. 4 can be modified to obtain a dual-beam interferometer, which is schematically shown in FIG. 5. It is essential here that the interference occurs between the individual measuring beams and not with reference radiation from a stationary reference arm, which does not comprise the specimen. Dashed lines designate a total degree of coupling of approximately 40% here. Each individual measuring beam is thus admixed here with a part of the respective other individual measuring beam.

In interferometer I having three individual measuring beams (N=3), for example, the individual measuring beam $M_1$ occurs at 40/3%, the individual measuring beam $M_2$ also at 40/3%, and the individual measuring beam M3 also at 40/3% at the output $A_1$. This applies in analogous manner for the further outputs.

The individual measuring beams are brought into superposition with each other and provided to the outputs A. Combined subregion signals may thus be detected, which have different phase relations between the subregion components. The analysis device 10 can thus detect quadrature components, in order to reduce mirror artifacts which may occur in Fourier domain OCT, for example. This applies similarly for the construction according to FIG. 4.

Only mutual interference between the subregion signals is detected in the construction of FIG. 5, so that the interference signals are independent of axial movement of the specimen P, because no interference occurs with radiation from stationary reference arms.

Figure 6:
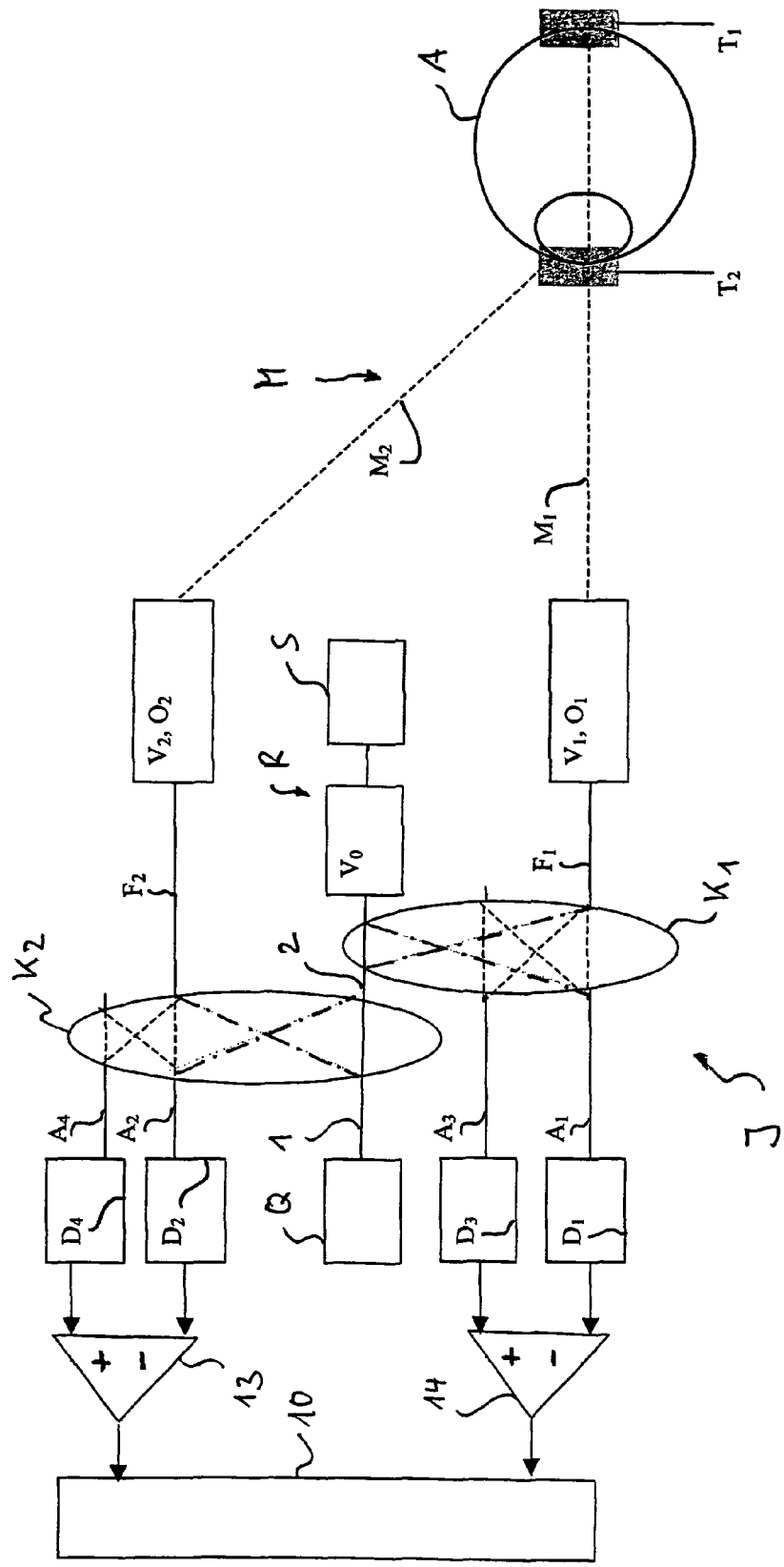
FIG. 6 depicts a schematic illustration similar to that of FIG. 4, but for an interferometer apparatus having balanced detection.

FIG. 6 shows a construction in which, on the one hand, the coupler K is implemented by two individual couplers $K_1$ and $K_2$. On the other hand, balanced detection is performed, as was already described for a different type of interferometer in US 2006/0109477 A1, which was already cited in this aspect. The principle of this balanced detection is, inter alia, that signals combined in pairs have a phase shift (e.g., approximately 180°), and thus a differential analysis using the differential amplifiers 13 and 14 eliminates any DC light components, e.g., variations of the intensity of the laser radiation source Q or interfering radiation. FIG. 6 shows the example for two measuring beams, a variant having three or more measuring beams is also possible, of course. FIG. 3 uses the same scheme as the prior figures in regard to the coupling factors, solid lines correspond to the total degree of coupling of 80% starting at the particular terminal, dashed lines to a total degree of coupling of 40% starting at the particular terminal, and dot-dash lines to a total degree of coupling of 20% starting at the particular terminal.

Figure 7:
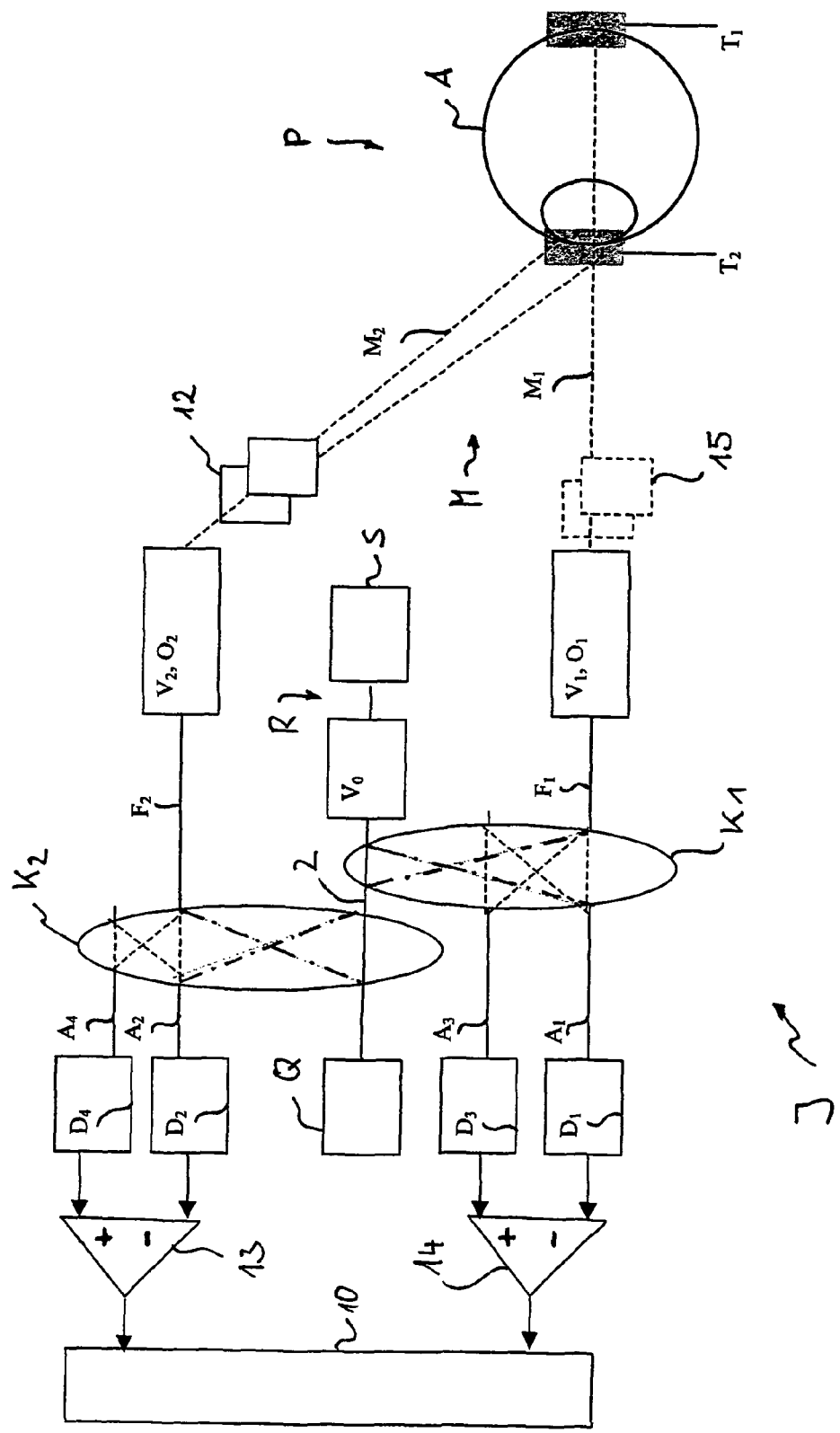
FIG. 7 depicts an interferometer apparatus similar to that of FIG. 6, but having additional lateral scanning of the specimen.

FIG. 7 shows a refinement in which a scanner 12 is provided in the measuring beam path, which laterally deflects an individual measuring beam, for example, in order to detect a three-dimensional region T. The combination with another individual measuring beam (for example, not deflected) thus allows a reference point to be detected to which the coordinate system of the three-dimensional deflection of the other specimen area can be related. Any axial movements of the specimen P, e.g., an eye, may thus be compensated for and do not result in corruption of the three-dimensional sampling.

In addition, the reference point can also be detected three-dimensionally not only with respect to its axial location, but rather by a further independent scanner provided in the individual measuring beam path of this individual measuring beam, so that three-dimensional movements of the specimen may be compensated for in measuring signals for another scanned specimen region.

The construction of FIG. 7 essentially implements the construction of FIG. 6, however, the individual measuring beam $M_2$ and optionally also the individual measuring beam $M_1$ are each deflected using an independent scanner 12 (and 15, respectively). The analysis unit 10 records the signals of the corresponding scanners and combines the signals output by the differential amplifiers 13 and 14 into an image corrected accordingly in regard to movements of the specimen under consideration of the scanner signals.

Figure 8:
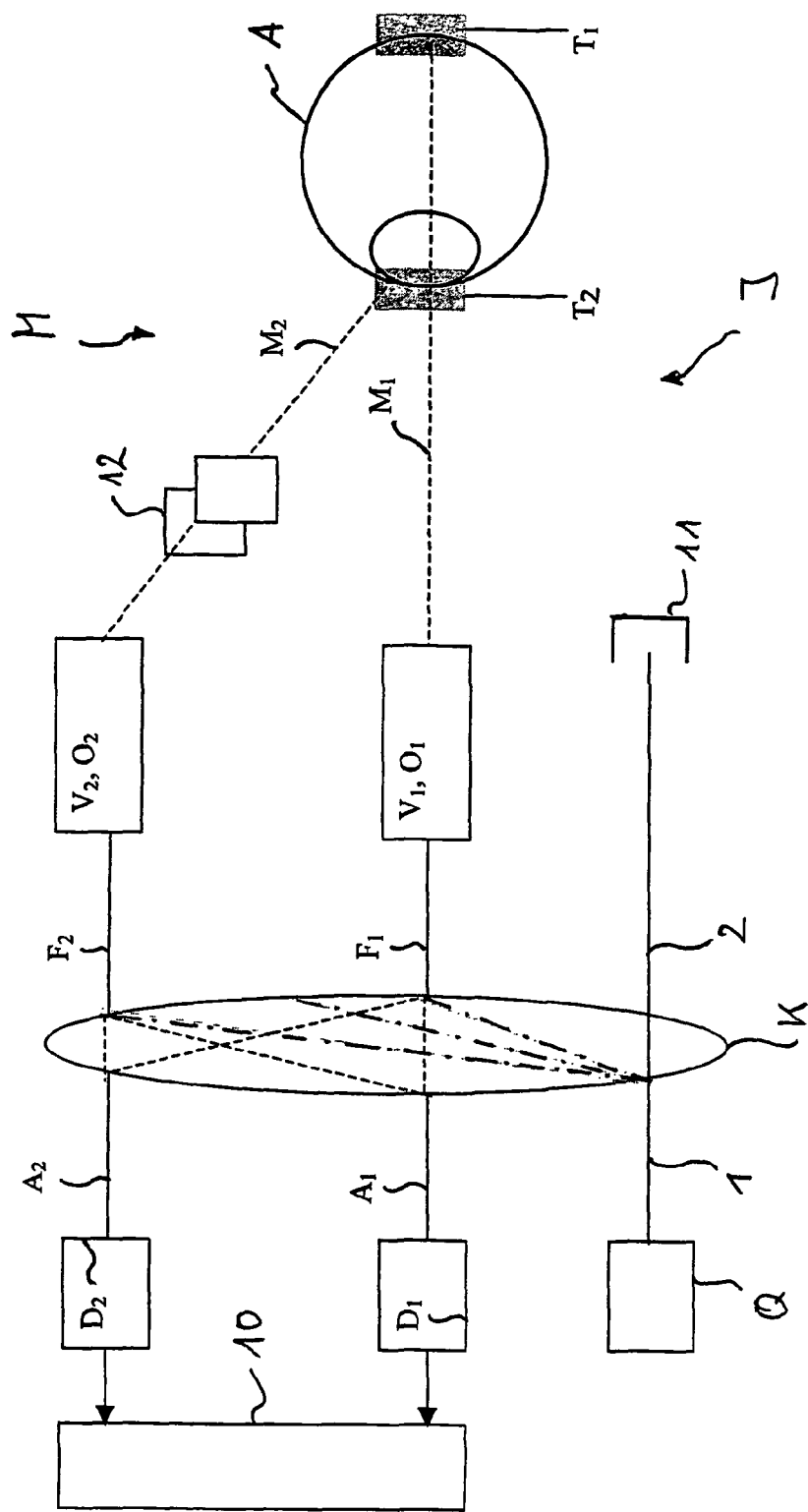
FIG. 8 depicts an interferometer apparatus similar to that of FIG. 7, but as a dual-beam interferometer.

Of course, this application of the scanner can also be used in any of the described interferometers I. This is schematically illustrated in FIG. 8, which shows the use of a scanner for a dual-beam approach. The scanning device is thus effective for at least one of the individual measuring beams. For ophthalmic applications this also allows imaging with respect to the eye lens including the determination of its eye lens shape (tilt of the lens, i.e., angle between optical axis and axis of vision, curvature of the posterior lens surface, curvature of the anterior lens surface). Imaging is also possible in the area of the retina, in particular in the area of the fovea.

The use of a static individual measuring beam aligned to the greatest corneal reflex is particularly advantageous in ophthalmic measurements, while a second individual measuring beam is laterally deflected for recording of the spatial distribution of retina structures, for example, for imaging (dual-beam OCT) or for determining the eye length with respect to specific reference points on the retina, is of particular advantage. For lateral scanning a simple determination of the frequency distribution of eye lengths also delivers information capable of characterizing an eye. These variants are important for cases of cataract, in which fixation is no longer possible for the patients and the eye length must be determined spatially resolved and/or statistically.

Figure 9B:
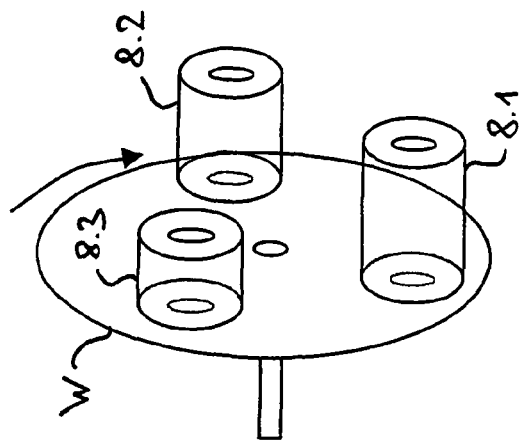
FIG. 9b depicts a revolver wheel having various beam splitter devices according to FIG. 9a, FIG. 10-12 depict schematic views of beam splitter devices in the interferometers of FIGS. 2-8, FIGS. 13-15 depict an OCDR interferometer similar to that of FIG. 1, the construction allowing exact balanced detection, the phase shift between the interference-readout detectors being exactly 180°.
Figure 9A:
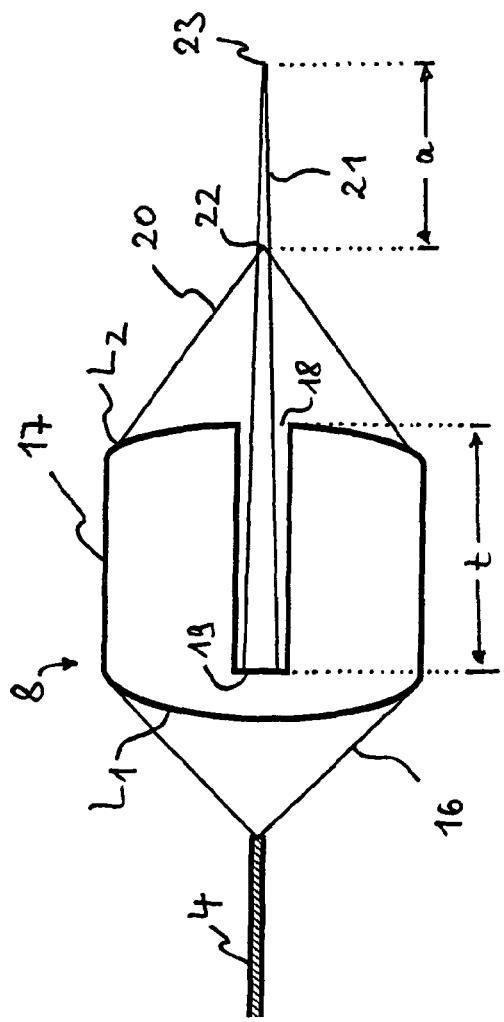
FIG. 9a depicts a schematic view of a beam splitter device in interferometer of FIG. 1.

Referring now to FIG. 9a, the construction of a monolithic beam splitter 8 is described. This beam splitter is used for the purpose of splitting a beam provided by an optical fiber 4 into two individual beams, which are axially offset to each another with respect to any later interference and are optionally also bundled in different foci spaced apart by a spacing a. In the return path, i.e., for radiation which propagates away from the specimen P, the beam splitter 8 reunites the measuring beam paths.

The beam splitter 8 receives a beam bundle 16, which exits at the end of the optical fiber 4, and collimates it using a first lens side $L_1$ comprised by a glass body 17 of the beam splitter 8. The radiation collimated in this manner then passes through the glass body 17, which has a pupil division on its output side. For this purpose, a hole 18 running along the optical axis is introduced in the opposing lens side $L_2$. The radiation exiting at the hole base 19 passes through a glass path which is less by the depth t of the hole 18 than the radiation which exits at the lens side $L_2$. This causes the delay of the individual beams to each another. The delay thus corresponds to the optical light path of the depth t of the hole 18 in the glass body 17 (of course, any material from which lenses can be made can also be used).

In FIG. 9a, the individual measuring beams exit in different focus cones 20, 21. This varying focusing is caused by different diffraction properties of the lens surface $L_2$ and the hole base 19. The varying diffraction properties of the pupil division thus achieved have the result that the foci 22, 23 are spaced apart by the spacing a. Focal distance and delays may be set independently of one another by the lens surfaces and the hole depth.

The focusing as shown in FIG. 9a is only to be understood as exemplary, of course. For example, if the hole base is implemented flat, the individual beam exiting in this pupil part can also be parallel, and/or have the same propagation direction caused by the lens surface $L_1$.

FIG. 9b shows that a change of the beam splitter 8 is also possible. For this purpose, the various beam splitters 8.1 and 8.2 and 8.3 are mounted on a revolver wheel W and the particular beam splitter required can be pivoted into the beam path. The various beam splitters 8.1, 8.2, and 8.3 differ in regard to the delay which is caused by the optical light path of the depth t.

Instead of an imaging beam splitter 8, a non-imaging beam splitter can also be used, if the first and second sides of the glass body 17 are not implemented as lens sides, but rather as flat.

Figure 11:
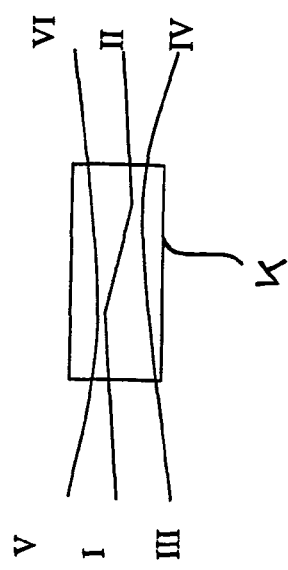
Figure 10:
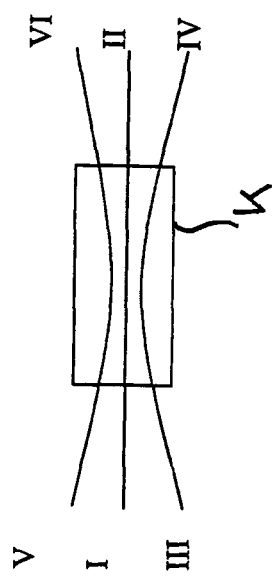
Figure 12:
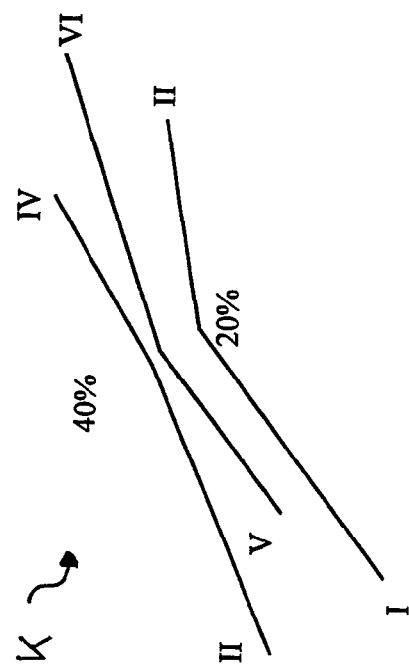

FIGS. 10 to 12 show schematic views of the fiber coupler K. A 3×3 coupler is shown in FIG. 10, which has terminals I-VI, and causes a corresponding coupling of I, III, and IV on the one side with II, IV, and VI on the other side.

FIG. 11 shows a modification of the fiber coupler K of FIG. 10, in which not three fibers are partially fused, but rather 2×2 fibers. As already described in US 2006/0109477 A1, which has already been cited multiple times from this aspect, a 3×3 coupler can thus be replaced.

If one uses such a combined 2×2 doublet, it is recommendable for cases of varying intensities of the individual measuring beams to guide the significantly stronger individual measuring beam via the route VI→V, as shown in the described embodiments, in order to avoid crosstalk in the more sensitive route IV→III. In interferometric measurements of the eye, the significantly stronger signal is typically that from the cornea, whereas the more sensitive signals originates from a measuring region which is on the retina.

For using balanced detection, a coupler K is advantageous, as shown in FIG. 12, which has a 40% cross coupling between VI→V and IV→III. The physical embodiment is shown in perspective in FIG. 12. The course of the coupling route V→IV thus lies folded above a plane which is spanned by the routes II→IV and I→II.

Figure 13:
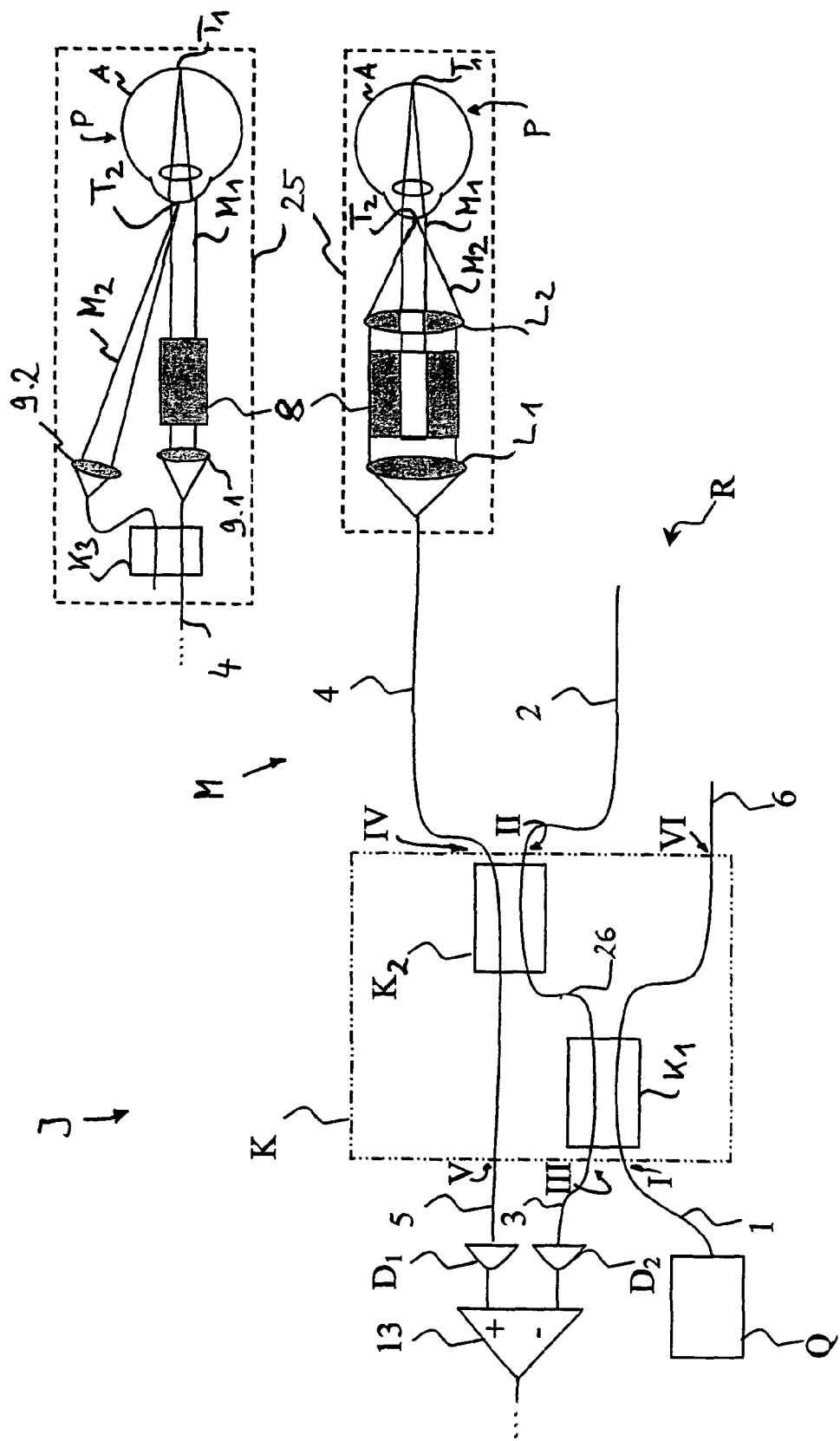
FIG. 13 depicts a construction having full balanced detection.

FIG. 13 shows a construction similar to that of FIG. 1, so-called exact balanced detection being able to be performed here, i.e., the mixture is composed symmetrically or proportionally.

In the construction of FIG. 13, it is illustrated, on the one hand, by a box drawn using dashed lines that the optical fiber 4 can very generally feed a varyingly implemented application module 25 situated, which splits the individual measuring beam paths from the measuring beam path which begins with the optical fiber 4. In the variant shown in the upper box in FIG. 13, a third coupler $K_3$ is used for this purpose, which performs splitting and combining of the individual measuring beam paths. The construction of the application module 25 of FIG. 13 shown in the lower box uses the beam splitter of FIG. 9a, but in the already described variant with optical surfaces on the part 8. The couplers $K_1$ and $K_2$ jointly implement a coupler K, which corresponds in principle to that in FIG. 1.

The coupler $K_2$ is implemented as a 50-50 coupler or splitter, whereby the mixtures in the optical fibers 5 and 3 are symmetrically composed, i.e., contain the radiation from the measuring beam paths $M_1$ and $M_2$ in equal parts each having a relative phase shift of 180° in relation to the superposition with the reference beam path.

Furthermore, the possibility exists through the construction of the coupler K from a 2×2 coupler doublet of using a connection optical fiber 26 between the couplers $K_1$ and $K_2$. This allows a type of circulator to be implemented. If the original radiation from the radiation source Q is linearly polarized and a quarter-wave unit is incorporated in the optical fiber 26, circularly polarized radiation reaches the measuring beam path M. The radiation returning through the optical fiber 26 to the optical fiber 1 and thus the source Q is polarized perpendicular to the original radiation as a result. This has proven to be positive for undisturbed and stable operation of the source Q. The optional use of a Faraday rotator in the light path 26 is also advantageous here, because an orthogonal polarization state with respect to the light coming from the light source in the light path 26 is achieved.

Figure 14:
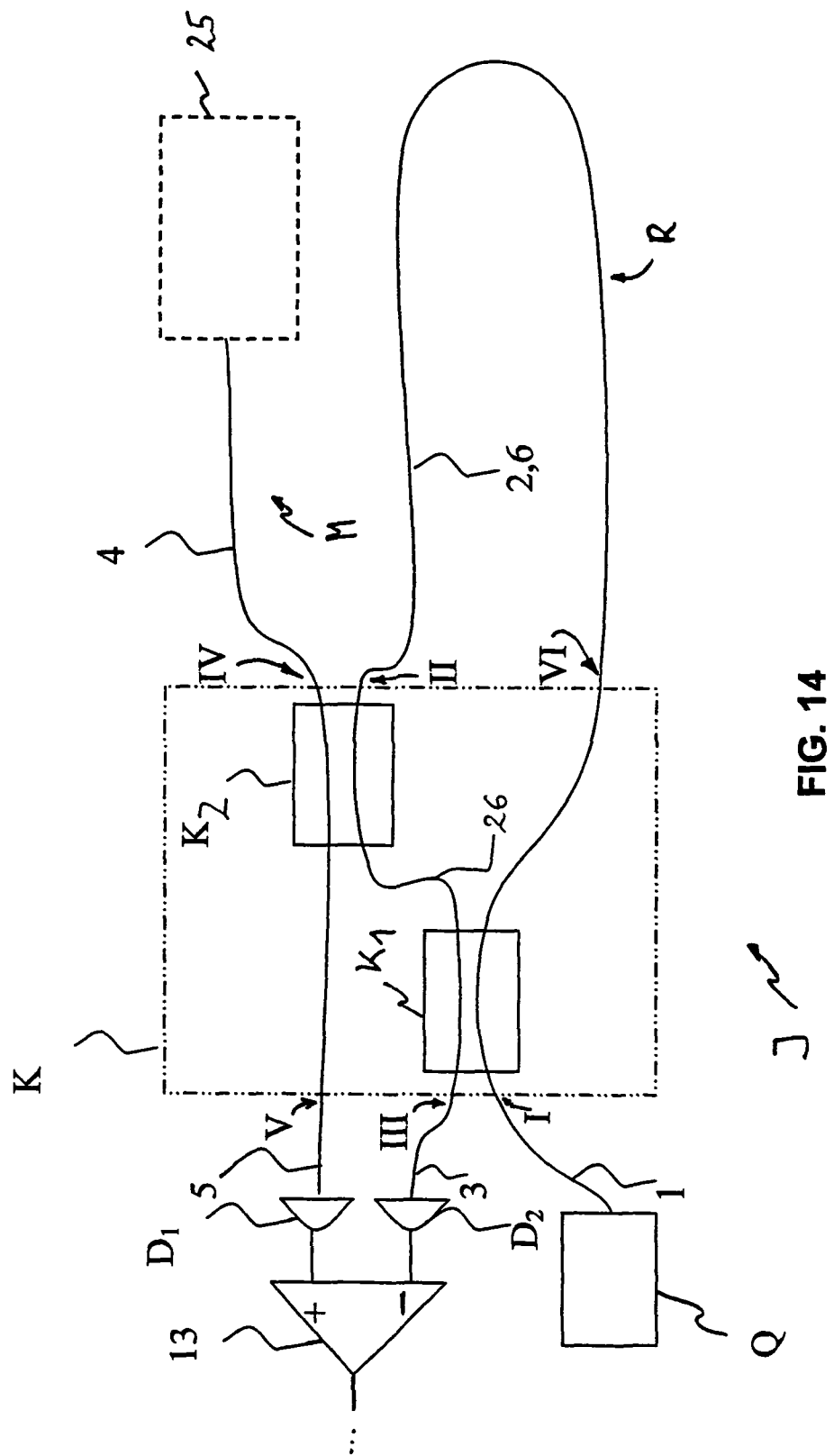
FIG. 14 depicts an alteration of the construction of FIG. 13 having a transmissive reference beam path.

FIG. 14 shows a modification of the construction of FIG. 13. The reference radiation is provided here by an optical fiber loop, i.e., a connection of the optical fibers 2 and 6. This can be designated as a transmissive reference. The transmissive reference arm can also contain fixed or variable attenuation elements for the purpose of testing the signal setting on the detectors or can be implemented such that a variable attenuation is realized. The statements made on FIG. 13 otherwise apply equally for the construction of FIG. 14.

Figure 15:
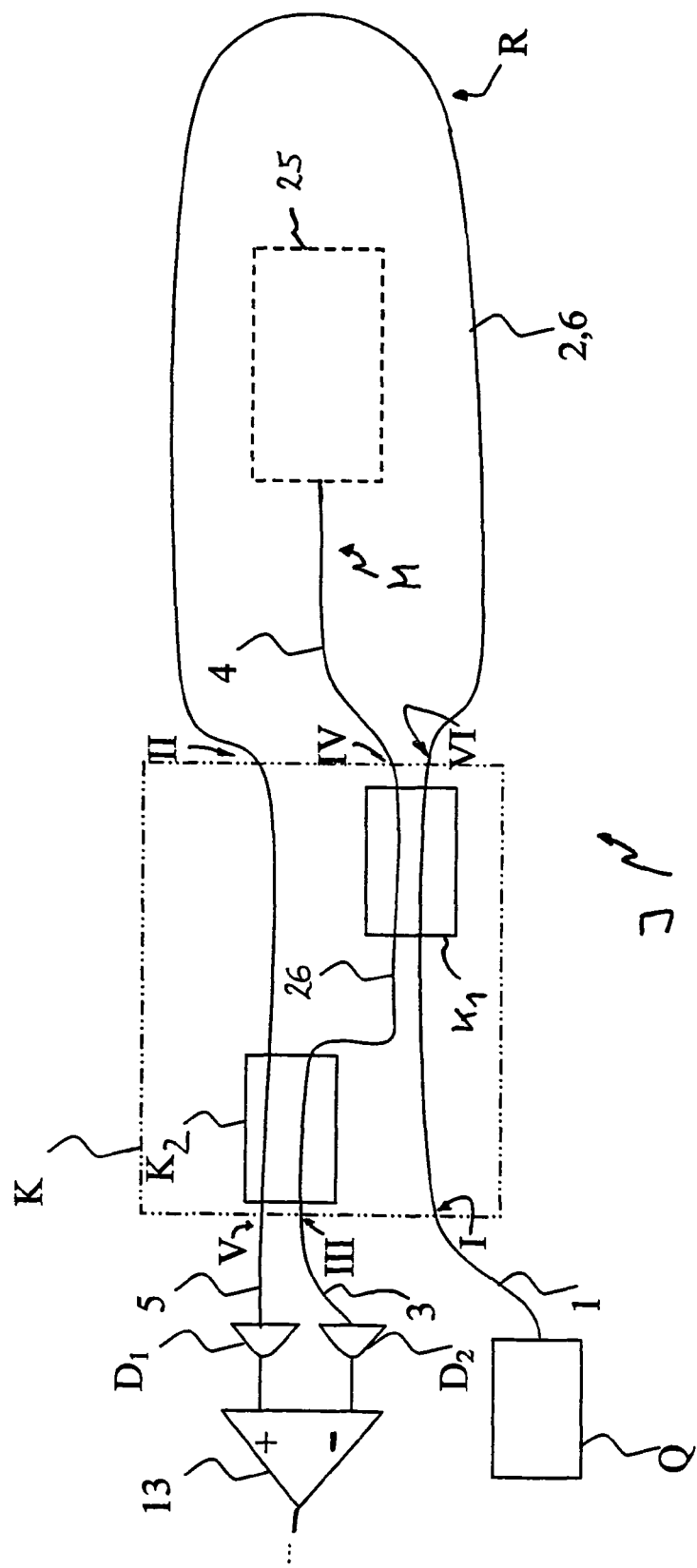
FIG. 15 depicts a construction similar to that of FIG. 14, but with a superposition device implemented differently.

Finally, the construction shown in FIG. 15 substantially corresponds to that of FIG. 14, but the couplers $K_2$ and $K_1$ are inverted in their sequence with respect to the connecting optical fiber 26. The original radiation again first reaches the coupler $K_2$, but goes from there directly into the measuring beam path and, of course, also into the reference beam path, which is again implemented as transmissive here.

Figure 16:
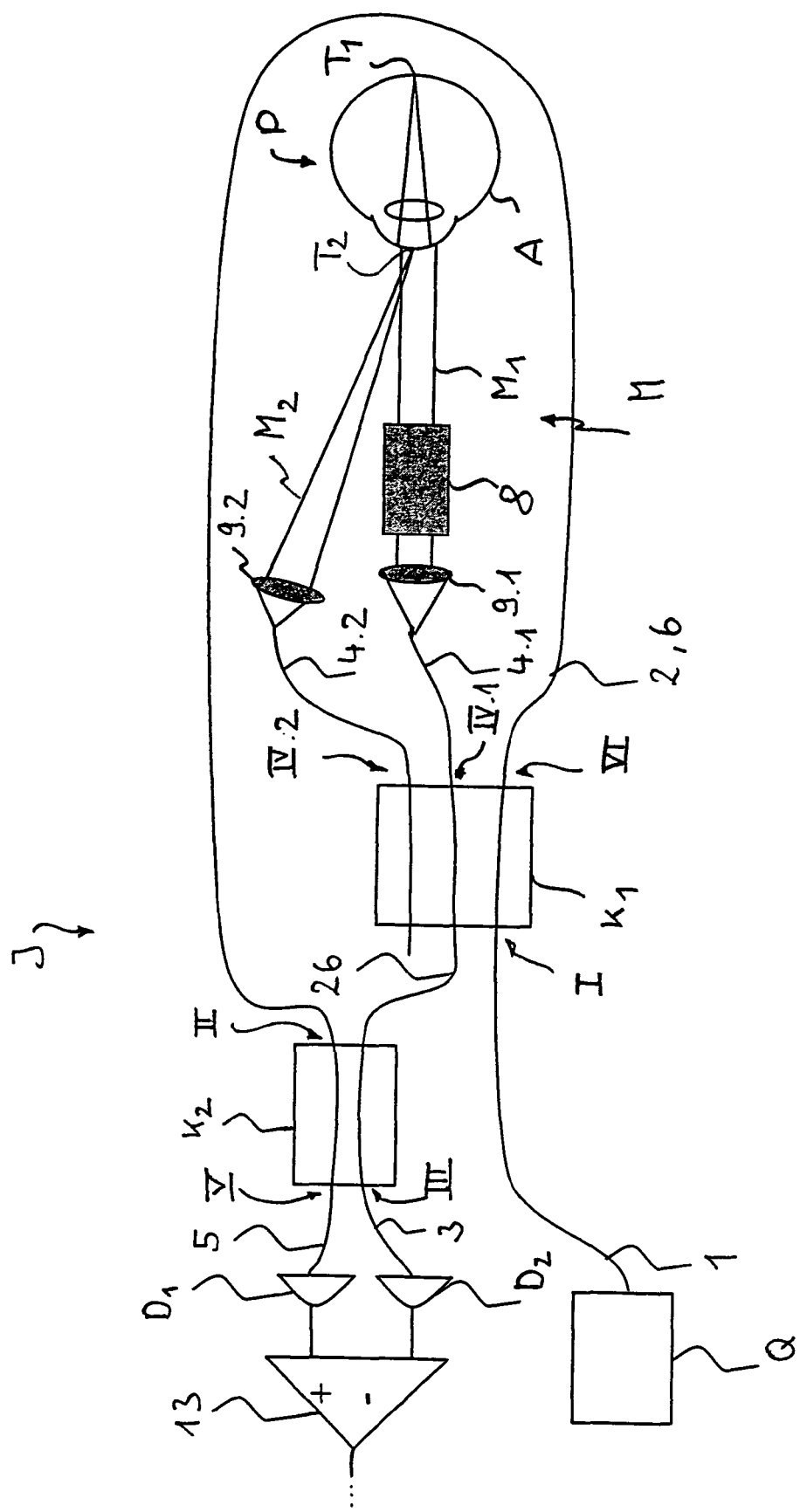
FIG. 16 depicts a construction similar to that of FIG. 15, but with two independent measuring beam paths.

Finally, FIG. 16 shows a construction similar to FIG. 15, but the coupler $K_1$ is constructed here as a 3×3 coupler, so that it splits by means of the terminals IV.1 and IV.2 directly into the two individual measuring beam paths.

As already noted, the individual measuring beam paths are adapted with respect to their optical paths to the spacing of the specimen regions to be detected. Besides a tuning of only the optical paths, the dispersions for the measuring beams can also be tuned separately to the conditions in the specimen. For this purpose, a suitable medium is introduced individually into the measuring beam paths, which influences the dispersion at unchanged optical delay so that influences of specimen areas which the measuring beams pass through are compensated for individually.

As also already noted, the embodiments described above can entirely fundamentally be implemented for SS, SD, or TD OCDR. In the latter case, tuning of the effective reference arm length is provided for. In the illustrations of FIGS. 1, 2, 6, 7, 13, 14, and 15, a device for adjusting the delay of the radiation in the reference beam path is additionally also provided in the reference beam path designated by R, for example, the RSOD already noted according to U.S. Pat. No. 6,654,127 or a path length adjustment. A similar element is provided in FIGS. 4 and 16 at the terminal of the optical fiber 2. Alternatively, it is also possible to perform a settable attenuation of the reference radiation in the reference arm, for example, using a variable optical attenuator (VOA) or doped fiber components. A very high attenuation can thus be readily achieved, which can additionally also be tuned. This represents both an alternative to the selection of more suitable fiber coupling ratios and also a supplementation for fine-tuning.

The invention claimed is:

1. A short coherence interferometer apparatus for measuring multiple axially spaced regions of a specimen, comprising:
   at least one measuring beam path, through which multiple individual measuring beams are incident on the specimen, and a single reference beam path, through which reference radiation is guided, the reference beam path having a single optical path length, the reference radiation being superimposed with the individual measuring beams, and being brought into interference with the individual measuring beams;
   wherein the individual measuring beams are axially offset relative to one another upon incidence on the specimen by an amount which is adapted to axial spacing between the axially spaced regions, and wherein the interferometer apparatus comprises a superposition device which superimposes each of the individual measuring beams returning from the specimen with the reference radiation to cause interference; and
   further wherein the superposition device comprises multiple outputs, each of the multiple outputs feeding a detector, wherein the superposition device receives the same reference radiation for superposition with all of the individual measuring beams and outputs a mixture of the multiple individual measuring beams superimposed with the reference radiation at each of the multiple outputs, each mixture containing fractions of the individual measuring beam, superimposed with the reference radiation in varying phasing.

2. The short coherence interferometer apparatus according to claim 1, further comprising a radiation source which provides measuring radiation that outputs a source beam, the source beam being fed to the superposition device which splits certain intensity fractions of the source beam into the measuring beam path and the reference beam path.

3. The short coherence interferometer apparatus according to claim 1, wherein the individual measuring beams have essentially equal components in each mixture.

4. The short coherence interferometer apparatus according to claim 1, further comprising a lens device in the measuring beam path, the lens device splitting measuring radiation into the individual measuring beams and delaying at least one individual measuring beam relative to one other individual measuring beam and focuses the individual measuring beams at different focal lengths to the specimen.

5. The short coherence interferometer apparatus according to claim 4, wherein the lens device splits the individual measuring beams by a pupil division, a separate pupil area of the lens device being associated with each individual measuring beam, with at least one imaging property selected from optical path lengths, pupil areas and dispersions of the pupil areas being different in the separate pupil areas.

6. The short coherence interferometer apparatus according to claim 5, the lens device comprising a refractive body having two lens surfaces and on only one lens side either a hole or a filling using a material having a different index of refraction, the hole or filling extending along an optical axis into the refractive body.

7. The short coherence interferometer apparatus according to claim 1, wherein the superposition device has one 3×3 fiber splitter or two combined 2×2 fiber splitters per pair of individual measuring beam paths.

8. The short coherence interferometer apparatus according to claim 1, wherein the superposition device conducts less than 50% of the intensity of the original beam into the measuring beam path and thus realizes less than 50% intensity loss for each individual measuring beam when superimposing the individual measuring beams and relaying them to the detectors.

9. The short coherence interferometer apparatus according to claim 1, wherein at least two of the detectors are read out in a differential analysis.

10. The short coherence interferometer apparatus according to claim 1, further comprising a polarization controller active for all individual measuring beams in the measuring beam path or a polarization controller in each individual measuring beam path, that equalizes the polarization states of the individual measuring beams to one another before the superposition of the individual measuring beams.

11. The short coherence interferometer apparatus according to claim 1, further comprising a swept radiation source and being adapted for SS OCDR.

12. The short coherence interferometer apparatus according to claim 11, wherein the axial offset of the individual measuring beams is greater than a measuring range defined by the swept radiation source.

13. The short coherence interferometer apparatus according to claim 1, further comprising at least one scanning device that scans the specimen by lateral relative displacement between the specimen and at least one of the individual measuring beams.

14. The short coherence interferometer apparatus according to claim 1, comprising a broadband radiation source and spectrally resolving detectors and being adapted for SD OCDR.

15. The short coherence interferometer apparatus according to claim 1, comprising a broadband radiation source and a reference arm having rapidly varying optical path length and being adapted for TD OCDR.

16. A short coherence interferometer apparatus for measuring multiple axially spaced regions of a specimen, comprising:
    at least one measuring beam path, through which multiple individual measuring beams are incident on the specimen, the individual measuring beams being axially offset to one another when incident on the specimen by an amount which is tuned to axial spacing between selected parts of the specimen;
    a detection device comprising two detectors;
    a superposition device, which superimposes at least two of the individual measuring beams with one another to cause interference;
    wherein the superposition device superimposes one of the two individual measuring beams on the other of the two individual measuring beams to cause interference and obtain two superimposed beams and then conducts each of the two superimposed beams to an associated one of the two detectors.

17. The short coherence interferometer apparatus according to claim 16, further comprising a lens device in the measuring beam path, the lens device splitting measuring radiation into the individual measuring beams and delaying at least one individual measuring beam relative to one other individual measuring beam and focuses the individual measuring beams at different focal lengths to the specimen.

18. The short coherence interferometer apparatus according to claim 17, wherein the lens device splits the individual measuring beams by a pupil division, a separate pupil area of the lens device being associated with each individual measuring beam, with at least one imaging property selected from optical path lengths, pupil areas and dispersions of the pupil areas being different in the separate pupil areas.

19. The short coherence interferometer apparatus according to claim 18, the lens device comprising a refractive body having two lens surfaces and on only one lens side either a hole or a filling using a material having a different index of refraction, the hole or filling extending along an optical axis into the refractive body.

20. The short coherence interferometer apparatus according to claim 16, wherein the superposition device has one 3×3 fiber splitter or two combined 2×2 fiber splitters per pair of individual measuring beam paths.

21. The short coherence interferometer apparatus according to claim 16, wherein the superposition device conducts less than 50% of the intensity of the original beam into the measuring beam path and thus realizes less than 50% intensity loss for each individual measuring beam when superimposing the individual measuring beams and relaying them to the detectors.

22. The short coherence interferometer apparatus according to claim 16, wherein at least two of the detectors are read out in a differential analysis.

23. The short coherence interferometer apparatus according to claim 16, further comprising a polarization controller active for all individual measuring beams in the measuring beam path or a polarization controller in each individual measuring beam path, that equalizes the polarization states of the individual measuring beams to one another before the superposition of the individual measuring beams.

24. The short coherence interferometer apparatus according to claim 16, further comprising a swept radiation source and being adapted for SS OCDR.

25. The short coherence interferometer apparatus according to claim 24, wherein the axial offset of the individual measuring beams is greater than a measuring range defined by the swept radiation source.

26. The short coherence interferometer apparatus according to claim 16, further comprising at least one scanning device that scans the specimen by lateral relative displacement between the specimen and at least one of the individual measuring beams.

27. The short coherence interferometer apparatus according to claim 16, comprising a broadband radiation source and spectrally resolving detectors and being adapted for SD OCDR.

28. The short coherence interferometer apparatus according to claim 16, comprising a broadband radiation source and a reference arm having rapidly varying optical path length and being adapted for TD OCDR.

* * * * *